US008703812B2

(12) United States Patent
Alkon

(10) Patent No.: US 8,703,812 B2
(45) Date of Patent: Apr. 22, 2014

(54) PROTEIN SYNTHESIS REQUIRED FOR LONG-TERM MEMORY IS INDUCED BY PKC ACTIVATION ON DAYS PRECEDING ASSOCIATIVE LEARNING

(75) Inventor: Daniel L. Alkon, Bethesda, MD (US)

(73) Assignee: Blanchette Rockefeller Neurosciences Institute, Rockville, MD (US)

( * ) Notice: Subject to any disclaimer, the term of this patent is extended or adjusted under 35 U.S.C. 154(b) by 0 days.

(21) Appl. No.: 13/561,770

(22) Filed: Jul. 30, 2012

(65) Prior Publication Data

US 2012/0289557 A1 Nov. 15, 2012

Related U.S. Application Data

(63) Continuation of application No. 12/851,222, filed on Aug. 5, 2010, now abandoned, which is a continuation of application No. 11/494,636, filed on Jul. 28, 2006, now abandoned.

(60) Provisional application No. 60/703,501, filed on Jul. 29, 2005, provisional application No. 60/728,753, filed on Oct. 21, 2005.

(51) Int. Cl.
*A01N 43/02* (2006.01)
*A61K 31/335* (2006.01)
*A01N 43/38* (2006.01)
*A61K 31/40* (2006.01)
*A01N 43/00* (2006.01)
*A61K 31/33* (2006.01)

(52) U.S. Cl.
USPC ............................ 514/450; 514/183; 514/410

(58) Field of Classification Search
USPC .......................................... 514/450, 183, 410
See application file for complete search history.

(56) References Cited

U.S. PATENT DOCUMENTS

| | | | |
|---|---|---|---|
| 4,560,774 A | 12/1985 | Pettit et al. | |
| 4,611,066 A | 9/1986 | Pettit et al. | |
| 4,833,139 A | 5/1989 | Martin | |
| 4,833,257 A | 5/1989 | Pettit et al. | |
| 5,072,004 A | 12/1991 | Pettit | |
| 5,196,447 A | 3/1993 | Pettit et al. | |
| 5,288,514 A | 2/1994 | Ellman | |
| 5,359,115 A | 10/1994 | Campbell et al. | |
| 5,362,899 A | 11/1994 | Campbell | |
| 5,393,897 A | 2/1995 | Pettit et al. | |
| 5,430,053 A | 7/1995 | Pettit | |
| 5,545,636 A * | 8/1996 | Heath et al. | 514/214.02 |
| 5,578,590 A | 11/1996 | Grunicke et al. | |
| 5,580,748 A | 12/1996 | Alkon et al. | |
| 5,625,232 A | 4/1997 | Numata et al. | |
| 5,770,593 A | 6/1998 | Grunicke et al. | |
| 5,891,870 A | 4/1999 | Driedger et al. | |
| 5,891,906 A | 4/1999 | Driedger et al. | |
| 5,955,501 A | 9/1999 | Driedger et al. | |
| 5,962,498 A | 10/1999 | Driedger et al. | |
| 5,962,504 A | 10/1999 | Kozikowski et al. | |
| 5,981,165 A | 11/1999 | Weiss et al. | |
| 6,043,270 A | 3/2000 | Driedger et al. | |
| 6,080,582 A | 6/2000 | Alkon et al. | |
| 6,080,784 A | 6/2000 | Driedger et al. | |
| 6,187,568 B1 | 2/2001 | Nishida et al. | |
| 6,242,479 B1 | 6/2001 | Wechter | |
| 6,407,058 B1 | 6/2002 | Staddon et al. | |
| 6,458,373 B1 | 10/2002 | Lambert et al. | |
| 6,624,189 B2 | 9/2003 | Wender et al. | |
| 7,977,377 B2 | 7/2011 | Sun et al. | |
| 2003/0050302 A1 | 3/2003 | Etcheberrigaray | |
| 2003/0077335 A1 | 4/2003 | Richardson et al. | |
| 2003/0171356 A1 | 9/2003 | Etcheberrigaray et al. | |
| 2003/0171385 A1 | 9/2003 | Alkon et al. | |
| 2005/0065205 A1 | 3/2005 | Alkon | |
| 2005/0075393 A1 | 4/2005 | Nishizaki et al. | |

FOREIGN PATENT DOCUMENTS

| | | |
|---|---|---|
| CA | 2401452 | 3/2003 |
| DE | A-3827974 | 2/1990 |
| DE | 19943198 | 3/2001 |
| EP | 0 115 472 | 8/1984 |
| EP | 0 324 574 A2 | 7/1989 |
| EP | 0 413 191 A1 | 2/1991 |
| EP | 0 432 856 | 6/1991 |
| EP | 1 195 159 | 4/2002 |
| JP | 06-279311 JP | 10/1994 |
| JP | 2001-240581 | 9/2001 |
| WO | WO 91/07087 | 5/1991 |
| WO | WO 92/10092 | 6/1992 |
| WO | WO 93/09668 | 5/1993 |
| WO | WO 93/20242 | 10/1993 |
| WO | WO 94/08051 | 4/1994 |

(Continued)

OTHER PUBLICATIONS

Wilkinson et al. (Biochem J 1993, 294, 335-337).*
Alkon et al., "Regulation of *Hermissenda* K+ Channels by Cytoplasmic and Membrane-Associated C-Kinase," J. Neurochem., 51(3):903-916 (1988).
Alkon et al., Protein Synthesis Required for Long-Term Memory is Induced by PKC Activation on Days Before Associative Learning, Proc. Natl. Acad. Sci. USA, 102:16432-16437 (2005).
Bennett et al., "Expression Analysis of BACE2 in Brain and Peripheral Tissues," The Journal of Biological Chemistry, 275( 27);29647-20651 (2000).

(Continued)

*Primary Examiner* — Sreeni Padmanabhan
*Assistant Examiner* — Uma Ramachandran
(74) *Attorney, Agent, or Firm* — Finnegan, Henderson, Farabow, Garret & Dunner

(57) ABSTRACT

The present invention provides methods of contacting a protein kinase C (PKC) activator with a PKC activator in a manner sufficient to stimulate the synthesis of proteins sufficient to consolidate long-term memory. The present invention also provides methods of contacting a protein kinase C (PKC) activator with a PKC activator in a manner sufficient to downregulate PKC.

7 Claims, 19 Drawing Sheets

(56) References Cited

FOREIGN PATENT DOCUMENTS

| WO | WO 96/35417 | 11/1996 |
|---|---|---|
| WO | WO 97/43268 | 11/1997 |
| WO | WO 98/32464 A1 | 7/1998 |
| WO | WO 99/59597 | 11/1999 |
| WO | WO 01/83449 | 8/2001 |
| WO | WO 01/68137 | 9/2001 |
| WO | WO 01/93883 | 12/2001 |
| WO | WO 02/50013 A1 | 6/2002 |
| WO | WO 02/083877 | 10/2002 |
| WO | WO 02/086106 | 10/2002 |
| WO | WO 02/097423 A3 | 11/2002 |
| WO | WO 03/075850 A2 | 9/2003 |
| WO | WO 03/075930 A1 | 9/2003 |
| WO | WO 2004/004641 A2 | 1/2004 |
| WO | WO 2004/047857 | 6/2004 |
| WO | WO 2006/031337 A2 | 3/2006 |
| WO | WO 2008/013573 | 1/2008 |
| WO | WO 2008/100449 | 8/2008 |

OTHER PUBLICATIONS

Bergamaschi et al., "Defective Phorbol Ester-Stimulated Secretion of B-Amyloid Precursor Protein from Alzheimer's Disease Fibroblasts," Neuroscience Letters, 201:1-4 (1995).

Bhagavan et al., "Restoration of TEA-Induced Calcium Responses in Fibroblasts from Alzheimer's Disease Patients by a PCK Activator," Neurobiol. Disease, 5:177-187 (1998).

Bondy et al., "The PHA-Induced Calcium Signal in Lymphocytes is Altered After Blockade of K+-Channels in Alzheimer's Disease," J. Psychiat. Res., 30(3):217-227 (1996).

Burke et al., "Update on Alzheimer's Disease: Promising advances in Detection and Treatment," Postgraduate Medicine, 106(5) (1999).

Burry, R. W., "PKC Activators (Phorbol Ester or Bryostatin) Stimulate Outgrowh of NGF-Dependent Neurites in a Subline of PC12 Cells," Journal of Neurosciences Research, 53:214-222 (1998).

Buxbaum et al., "Evidence That Tumor Necrosis Factor a Converting Enzyme Is Involved in Regulated a-Secretase Cleavage of the Alzheimer Amyloid Protein Precursor," The Journal of Biological Chemistry, 273(43):27765-27767 (1998).

Cai et al., "BACE1 is the major β-secretase for Generation of Aβ Peptides by Neurons." Nature Neuroscience, 4(3):233-234 (Mar. 2001).

Caputi et al., "Increased Secretion of the Amino-Terminal Fragment of Amyloid Precursor Protein in Brains of Rats with a Constitutive Up-Regulation of Protein Kinase C," J. Neurochem., 68(6):2523-2529 (1997).

Certified Application of International Application Serial No. PCT/US03/07101, 2003.

Certified U.S. Appl. No. 60/392,951, 2002.

Cole et al., "Decreased Levels of Protein Kinase C in Alzheimer Brain," Brain Research, 452:165-174 (1988).

Connolly, "Fibroblast Models of Neurological Disorders: Fluorescence Measurement Studies," TIPS, 19:171-177 (1998).

Coughlan et al., "Factors Influencing the Processing and Function of the Amyloid B Precursor Protein—A Potential Therapeutic Target in Alzheimer's Disease?," Pharmacology & Therapeutics, 86:111-144 (2000).

Desdouits et al., "Amyloid β Peptide Formation in Cell-free Preparations," The Journal of Biological Chemistry, 271(40):24670-24674 (1996).

Efthimiopoulos et al., "Intracellular Cyclic AMP Inhibits Constitutive and Phorbol Ester-Stimulated Secretory Cleavage of Amyloid Precursor Protein," J. Neurochem., 67(2):872-875 (1996).

English-language Translation for JP 6-279311 dated Jun. 2008.

English-language Translation for JP 2001-240581, 2001.

Esler et al., "A Portrait of Alzheimer Secretases—New Features and Familiar Faces," Science, 293:1449-1454 (2001).

Espacenet English Abstract for EP 0 115 472 (2012).

Etcheberrigaray et al., "Calcium Responses are Altered in Fibroblasts from Alzheimer's Patients and Pre-symptomatic PS1 Carriers; a Potential Tool for Early Diagnosis," Alzheimer's Reports, 3(5&6):305-312 (2000).

Etcheberrigaray et al., "Therapeutic effects of PKC activators in Alzheimer's disease transgenic mice", PNAS, 01(30):11141-11146 (2004).

Favit et al., "Alzheimer's-specific effects of soluble β-amyloid on protein kinase C- and -degradation in human fibroblasts", Cell Biology, 95:5562-5567 (1998).

Final Office Action mailed Nov. 23, 2010, in U.S. Appl. No. 11/802,842.

Final Office Action mailed Mar. 5, 2009, in U.S. Appl. No. 10/933,536.

Final Office Action mailed May 13, 2010, in U.S. Appl. No. 12/068,742.

Gabuzda et al., "Inhibition of β-Amyloid Production by Activation of Protein Kinase C," J. Neurochem., 61(6):2326-2329 (1993).

Gillespie et al., "Secretory Processing of the Alzheimer Amyloid B/A4 Protein Precursor is Increased by Protein Phosphorylation," Biochemical and Biophysical Research Communications, 187(3):1285-1290 (1992).

Goekjian, et al., "Protein Kinase C in the Treatment of Disease: Signal Transduction Pathways, Inhibitors, and Agents in Development," Current Medicinal Chemistry, 6:877-903 (1999).

Govoni et al., "Cytosol Protein Kinase C Downregulation in Fibroblasts from Alzheimer's Disease Patients," Neurology, 43:2581-2586 (1993).

Govoni et al., "Fibroblasts of Patients Affected by Down's Syndrome Oversecrete Amyloid Precursor Protein and are Hyporesponsive to Protein Kinase C Stimulation," Neurology, 46:1069-1075 (1996).

Hanui et al., "Characterization of Alzheimer's β-Secretase Protein BACE," The Journal of Biological Chemistry, 275(28):21099-21106 (2000).

Hardy, "Amyloid, the Presinilins and Alzheimer's Disease," TINS, 20(4): 154-159 (1997).

Hardy, "Molecular Genetics of Alzheimer's Disease," Acta Neural Scand, Supplemental, 165:13-17 (1996).

Hennings et al., "Bryostatin 1, an Activator of Protein Kinase C, Inhibits Tumor Promotion by Phorbol Esters in SENCAR Mouse Skin," Carcinogenesis, 8(9):1343-1346 (1987).

Hofmann, "The Potential for Isoenzyme-Selective Modulation of Protein Kinase C," The FASEB Journal, 11:649-669 (1997).

Hung et al., "Activation of Protein Kinase C Inhibits Cellular Production of the Amyloid β-Protein," The Journal of Biological Chemistry, 268(31):22959-22962 (1993).

Huynh et al., "Reduced Protein Kinase C Immunoreactivity and Altered Protein Phosphorylation in Alzheimer's Disease Fibroblasts," Arch Neural 46 (1989).

Ibarreta et al., "Benzolactam (BL) Enhances sAPP Secretion in Fibroblasts and in PC12 Cells," Ageing, 10(5):1035-1040 (1999).

Jin et al., "Changes in Protein Kinases in Brain Aging and Alzheimer's Disease," Drugs &Aging, 6(2):136-149 (1995).

Jolly-Tornetta et al., "Protein Kinase C Regulation of Intracellular and Cell Surface Amyloid Precursor Protein (APP) Cleavage in CH0695 Cells," Biochemistry, 39:15282-15290 (2000).

Kanno et al., "The Linoleic Acid Derivative DCP-LA Selectively Activates PKC-ϵ, Possibly Binding to the Phosphatidylserine Binding Site," Journal of Lipid Research, 47:1146-56 (2006).

Kanno et al., "The Newly Synthesized Linoleic Acid Derivative DCP-LA Selectively Activates PKC-ϵ", Dept. of Physiology, Hyogo College of Med., Hyogo, Japan, p. 552 (2006).

Khan et al., "An Internally Controlled Peripheral Biomarker for Alzheimer's Disease: Erk1 and Erk2 responses to the Inflammatory Signal Bradykinin," PNAS, vol. 103, No. 35, pp. 13203-13207, Aug. 29, 2006.

Kim et al, Amyloid Precursor Protein Processing is Separately Regulated by Protein Kinase C and Tyrosine Kinase in Human Astrocytes, Neurosci. Letters, 324(3):184-188 (May 2002).

Kinouchi et al., "Conventional Protein Kinase C (PKC)-α and Novel PKCϵ, But Not -δ, Increase the Secretion of an N-Terminal Fragment of Alzheimer's Disease Amyloid Precursor Protein from PKC cDNA Transfected 3Y1 Fibroblasts," FEBS Letters, 364:203-206 (1995).

(56) References Cited

OTHER PUBLICATIONS

Kozikowski et al., "Modeling, Chemistry, and Biology of the Benzolactam Analogues of Indolactam V (ILV). 2. Identification of the Binding Site of the Benzolactams in the CRD2 Activator-Binding Domain in PKCs and Discovery of an ILV Analogue of Improved Isozyme Selectivity," J. Med. Chem.,40:1316-1326 (1997).
Maiorini et al., "Potential Novel Targets for Alzheimer Pharmacotherapy: I. Secretase," Journal of Clinical Pharmacy and Therapeutics, 27:169-183 (2002).
Masliah et al., "Role of Amyloid Precursor Protein in the Mechanisms of Neurodegeneration in Alzheimer's Disease," Laboratory Investigation, 77(3):197-209 (1997).
Masliah, "Protein Kinase C Alteration Is an Early Biochemical Marker in Alzheimer's Disease," The Journal of Neuroscience, 11(9): 2759-2767 (1991).
Mutter et al., "Chemistry and Clinical Biology of the Bryostatins," Bioorganic & Medicinal Chemistry, 8:1841-1860 (2000).
Nagata et al., "FR236924, a Newly Synthesized Derivataive of Linoleic Acid, Ameliorates Memory Deficits in Rats Intraventricularly Injected with Amyloid-Beta Peptide." Jpn. J. Physiol. 53,Suppl. 2003(319): S261.
Nagata et al., "The Newly Synthesized Linoleic Acid Derivative CP-LA Ameliorates Memory Deficits in Animal Dmodels Treated with Amyloid-β Peptide and Scopolamine", Psychogeriatrics, 5:22-126 (2003).
Nan et al., "Dual Function Glutamate-Related Ligands: Discovery of a Novel, Potent Inhibitor of Glutamate Carboxypeptidase II Possessing mGluR3 Agonist Activity," Journal of Medicinal Chemistry, 43(5):772-774 (2000).
NME Digest, Drug News Perspect, 2002, pp. 666-674, vol. 15, No. 10.
Office Action mailed Jan. 30, 2008, in U.S. Appl. No. 10/933,536.
Office Action mailed May 26, 2010, in U.S. Appl. No. 11/802,842.
Office Action mailed May 28, 2008, in U.S. Appl. No. 10/933,536.
Office Action (Restriction Requirement) mailed Jun. 23, 2009, in U.S. Appl. No. 12/068,742.
Office Action mailed Feb. 4, 2010, in U.S. Appl. No. 11/802,842.
Office Action mailed Jan. 31, 2012, issued in U.S. Appl. No. 12/851,222.
Office Action mailed Oct. 21, 2009, in U.S. Appl. No. 12/068,742.
Robner et al., "Short Communication: Protein Kinase Cα and β1 Isoforms are Regulators of α-Secretary Proteolytic Processing of Amyloid Precursor Protein in Vivo," European Journal of Nueuroscience, 13:1644-1648 (2001).
Savage et al., "Turnover of Amyloid β-Protein in Mouse Brain and Acute Reduction of Its Level by Phorbol Ester," The Journal of Neuroscience, 18(5):1743-1752 (1998).
Scheuner et al., "Secreted Amyloid β-Protein Similar to that in the Senile Plaques of Alzheimer's Disease is Increased in Vivo by the Presenilin 1 and 2 and APP Mutations linked to Familial Alzheimer's Disease," Nature Medicine, 2(8) (1996).
Selkoe, "Alzheimer's Disease: Genes, Proteins, and Therapy," Physiological Reviews, 81(2):741-766 (2001).
Selkoe, "Normal and Abnormal Biology of the β-Amyloid Precursor Protein," Annu. Re. Neurosci., 17:489-517 (1994).
Selkoe, "Translating Cell Biology into Therapeutic Advances in Alzheimer's Disease," Nature, 399(24):A23-A31 (1999).
Shimohama et al., "Assessment of Protein Kinase C Isozymes by Two-Site Enzyme Immunoassay in Human Brains and Changes in Alzheimer's Disease," Neurology, 43:1407-1413 (1993).
Shoulson, "Experimental Therapeutics of Denegerative Disorders: Unmet Needs," Science, 282:1072-1074 (1998).
Sinha et al., "Purification and Cloning of Amyloid Precursor Protein β-Secretase from Human Brain," Nature, 402:537-540 (1999).
Skovronsky et al., Protein Kinase C-Dependent α-Secretase Competes with β-Secretase for Cleavage of Amyloid-β Precursor Protein in the Trans-Golgi Network, The Journal of Biological Chemistry, 275(4):2568-2575 (2000).

Small et al., "Alzheimer's Disease and the Amyloid β. Protein: What is the Role of Amyloid?," Journal of Neurochemistry, 73(2):443-449 (1999).
Supplemental Partial European Search Report for EP03742389 dated Sep. 12, 2007.
Szallasi et al., "Differential Regulation of Protein Kinase C Isozymes by Cryostatin 1 and Phorbol 12-Myristate 13-Acetate in NIH 3T3 Fibroblasts," Journal of Biological Chemistry, 269(3):2118-2124 (1994).
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).
Tanzi et al., "The Gene Defects Responsible for Familial Alzheimer's Disease," Neurolobiology of Disease, 3:159-168 (1996).
Turner et al., "Specificity of Memapsin 1 and Its Implications on the Design of Memapsin 2 (β-Secretase) Inhibitor Selectivity," Biochemistry, 41:8742-8746 (2002).
Varterasian et al., "Phase II Trial of Bryostatin 1 in Patients with Relapsed Low-Grade Non-Hodgkin's Lymphoma and Chronic Lymphocytic Leukemia," Clinical Cancer Research, vol. 6, pp. 825-828, 2000.
Vassar et al., "A-Generating Enzymes; Recent Advances in Band γ-Secretase Research," Neuron, 27:419-422 (2000).
Vassar et al., "Secretase Cleavage of Alzheimer's Amyloid Precursor Protein by the Transmembrane Aspartic Protease BACE," Science, 286:735-741 (1999).
Wang et al., "Attenuated Protein Kinase C Activity and Translocation in Alzheimer's Disease Brain," Neurobiology of Aging, 15(3):293-298 (1994).
Webb et al., "Protein Kinase C Isoenzymes: A Review of Their Structure, Regulation and Role in Regulating Airways Smooth Muscie Tone and Mitogenesis," British Journal of Pharmacology, vol. 30, pp. 1433-1452, 2000.
Wiltfang et al., "Molecular Biology of Alzheimer's Dementia and Its Clinical Relevance to Early Diagnosis and New Therapeutic Strategies," Gerontology, 47:65-71 (2001).
Xu et al., "Metabolism of Alzheimer β-Amyloid Precursor Protein; Regulation by Protein Kinase A in Intact Cells and in a Cell-Free System," Proc. Natl. Acad. Sci. USA, 93:4081-4084 (1996).
Yaguchi et al., "Effects of Cis-unsaturated Free Fatty Acids on PKC-ε Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1):105-108 (Jan. 23, 2006).
Yamamoto et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, 130:207-213 (2005).
Zhang et al., "Preclinical Pharmacology of the Natural Product Anticancer Agent Bryostatin 1, an Activator of Protein Kinase C1," Cancer Research, 56:802-808 (1996).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).
Agranoff et al., "Actinomycin D Blocks Formation of Memory of Shock-Avoidance in Goldfish," Science, 158 (Dec. 22, 1967).
Bank et al., "Classical Conditioning Induces Long-Term Translocation of Protein Kinase C in Rabbit Hippocampal CA1 Cells", Proc. Natl. Acad. Sci. USA, 85:1988-1992 (Mar. 1988).
Bergold et al., "Protein Synthesis During Acquisition of Long-Term Facilitation is Needed for the Persistent Loss of Regulatory Subunits of the Aplysia cAMP-Dependent Protein Kinase", Proc. Natl. Acad. Sci. USA, 87:3788-3791(May 1990).
Cavallaro "Memory-Specific Temporal Profiles of Gene Expression in the Hippocampus", PNAS, 99( 25):16279-16284 (Dec. 2002).
Crow et al., "Inhibition of Protein Synthesis Blocks Long-Term Enhancement of Generator Potentials Produced by One-Trial in Vivo Conditioning in *Hermissenda*", Proc. Natl. Acad. Sci. USA, 87:4490-4494 (Jun. 1990).

(56) References Cited

OTHER PUBLICATIONS

Crow et al., "Protein Synthesis-Dependent and mRNA Synthesis-Independent Intermediate Phase of Memory in *Hermissenda*," The American Physiological Society, Rapid Communication, 495-500 (1999).
Epstein et al., "Time Windows for Effects of Protein Synthesis Inhibitors on Pavlovian Conditioning in *Hermissenda*: Behavioral Aspects", Neurobiology of Learning and Memory, 79:127-131 (2003).
Ezzeddine et al., "Prolonged Habituation of the Gill-Withdrawal Reflex in Aplysia Depends on Protein Synthesis, Protein Phosphase Activity, and Postsynaptic Glutamate Receptors," The Journal of Neuroscience, 23(29):9585-9594 (Oct. 22, 2003).
Farley et al., "Protein Kinase C Inhibitors Prevent Induction and Continued Expression of Cell Memory in *Hermissenda* Type B Photoreceptors", Proc. Natl. Acad. Sci. USA, 88:2016-2020 (Mar. 1991).
Flexner et al., "Effect of Acetoxycyclohemimide and of an Acetoxycycloheximide-Puromycin Mixture on Cerebral Protein Synthesis and Memory in Mice," Proc. N.A.S., 55:369-374 (1966).
Hyden et al., "Brain-Cell Protein Synthesis Specifically Related to Learning", Proceedings of the National Academy of Sciences, 65(4):898-904, (Apr. 1970).
Kuzirian et al., "Bryostatin Enhancement of Memory in *Hermissenda*", Biol. Bull. 210:201-214 (Jun. 2006).
Kuzirian et al., "Pavlovian Conditioning-Specific Increases of the Ca2+-and GTP-Binding Protein, Calexcitin in Identified *Hermissenda* Visual Cells", Journal of Neurocytology, 30:993-1008 (2001).
Leontieva et al., "Identification of Two Distinct Pathways of Protein Kinase Ca Down-regulation in Intestinal Epthelial Cells", The Journal of Biological Chemistry, 279(7):5788-5801 (2004).
Lieb et al., "Valproic Acid inhibits substance P-induced Activation of Protein Kinase C Epsilon and Expression of the Substance P Receptor," Journal of Neurochemistry, 86:69-76 (2003).
Lu et al., "Activation of Protein Kinase C Triggers Its Ubiquitination and Degradation," Molecular and Cellular Biology, 18(2): 839-845 (Feb. 1983).
Marshall et al., "Phase 1 Study of Prolonged Infusion Bryostatin-1 in Patients with Advanced Malignancies", Cancer Biology & Therapy 1:4, 409-416 (Jul./Aug. 2002).
McPhie et al., "Cell Specificity of Molecular Changes During Memory Storage", Journal of Neurochemistry, 60( 2):646-651 (1993).
Nelson et al., "Isolation of a G Protein That Is Modified by Learning and Reduces Potassium Currents in *Hermissenda*," Science, 247:1479-1483 (Mar. 23, 1990).
Nelson et al., "Specific High Molecular Weight mRNAs Induced by Associative Learning in *Hermissenda*", Proc. Nat. Acad. Sci. USA, 87:269-273 (Jan. 1990).
Olds et al., "Discrimination Learning Alters the Distribution of Protein Kinase C in the Hippocampus of Rats," The Journal of Neurosciences, 10(11 ):3707-3713 (Nov. 1990).
Olds et al., "Imaging of Memory-Specific Changes in the Distribution of Protein Kinase C in the Hippocampus", Science, 245:866-869 (Aug. 25, 1989).
Prevostel et al., "Protein Kinase Ca Actively Downregulates Through Caveolae-Dependent Traffic to an Endosomal Compartment," Journal of Cell Science, 113:2575-2584 (2000).
Quattrone et al., "Posttranscriptional Regulation of Gene Expression in Learning by the Neuronal ELAV-Like mRNA- Stabilizing Proteins", PNAS, vol. 98, No. 20, pp. 11668-11673, Sep. 25, 2001.
Scioletti et al., "Memory Enhancement by Bryostain in *Hermissenda*", Biol. Bull., 207, (Oct. 2004) p. 159.
Sun et al., "Dual Effects of Bryostatin-1 on Spatial Memory and Depression", Eur. J. Pharmacol., vol. 512, pp. 43-51, 2005.
Talk et al., "Neurophysiological Substrates of Context Conditioning in *Hermissenda* Suggest a Temporally Invariant Form of Activity-Dependent Neuronal Facilitation", Neurobiology of Learning and Memory, 72:95-117 (1999).

Zhao et al., "Spatial learning induced changes in expression of the ryanodine type II receptor in the rat hippocampus," The FASEB Journal, vol. 14, pp. 290-300, Feb. 2000.
Abramets et al., "Behavioral Depression-Related Modifications of the Properties of Glutamatergic Synapses in the Basolateral Amygdalar Nucleus in Rats," Neurophysiology, 34(4):283-293 (2002).
Alkon, D.L., "Calcium-mediated reduction of ionic currents: A biophysical memory trace." Science, vol. 226, pp. 1037-1045, 1984.
Barbas et al., "Multiple Serotonergic Mechanisms Contributing to Sensitization in Aplysia: Evidence of Diverse Serotonin Receptor Subtypes," Serotonin & Memory/Review, 10:373-386, 2003.
Battaini, "Protein Kinase C Isoforms as Therapeutic Targets in Nervous System Disease States," Pharmacological Research, 44(5):353-361 (2001).
Berke et al., "Dopamine and Glutamate Induce Distinct Striatal Splice Forms of Ania-6, an RNA Polymerase II-Associated Cyclin," Neuron, 32:277-287 (Oct. 25, 2001).
Berman et al., "Specific and Differential Activation of Mitogen-Activated Protein Kinase Cascades by Unfamiliar Taste in the Insular Cortex of the Behaving Rat," The Journal of Nueroscience, 18(23);10037-10044 (Dec. 1, 1998)
Besag, "Behavioral Effects of the New Anticonvulsants," Drug Safety, 24(7):513-536 (2001).
Bouron et al. "Acute Application of the Tricyclic Antidepressant Desipramine Presynaptically Stimulates the Exocytosis of Glutamate in the Hippocampus," Neuroscience, 90(3):729-736, (1999).
Budziszewska et al., "Antidepressant Drugs Inhibit Glucocorticoid Receptor-Mediated Gene Transcription—A Possible Mechanism," British Journal of Pharmacology, 130, 1385-1393 (2000).
Calo et al., "Pharmacology of Nociceptin and its Receptor: a Novel Therapeutic Target", British Journal of Pharmacology, 129:1261-1283 (2000).
Casini et al., "Carbonic Anhydrase Activators. The Selective Serotonin Reuptake Inhibitors Fluoxetine, Sertraline and Citalopram Are Strong Activators of Isozymes I and II," Bioorganic & Medicinal Chemistry Letters, 13:2765-2768 (2003).
Cavallaro et al., "Late Memory-Related Genes in the Hippocampus Revealed by RNA Fingerprinting", Proc. Natl. Acad. Sci. USA, 94:9669-9673 (Sep. 1997).
Chetkovich et al., "N-Methyl-D-Aspartate Receptor Activation increases cAMP Levels and Voltage-Gated Ca2+ Channel Activity in Area CA1 of Hippocampus", Proc. Natl. Acad. Sci. USA, 88:6467-6471 (Aug. 1991).
Coull et al., "Altered Brain Protein Kinase C in Depression: a Post-Mortem Study," European Neuropsychopharmacology, 10:283-288 (2000).
Davis, "The Mitogen-activated Protein Kinase Signal Transduction Pathway," The Journal of Biological Chemistry, 268(20):14553-14556 (Jul. 15, 1993).
English Translation for JP 2001-240581 (2012).
English language abstract of DE 19943198, 2001.
Ferrari, "Behavioural Pharmacology of Imidazole, a Potential Antidepressant Agent," Arch. Int. Pharmacodyn, 277:303-312 (1985).
Gomez et al., "Ca2+ Signaling via the Neuronal Calcium Sensor-1 Regulates Associative Learning and Memory in *C. elegans*," Neuron, 30:241-248 (Apr. 2001).
Gould et al., "Signaling Networks in the Pathophysiology and Ttreatment of Mood Disorders," Journal of Psychosomatic Research, 53:687-697 (2002).
Hahn et al., "Abnormalities in Protein Kinase C Signaling and the Pathphysiology of Bipolar Disorder," Bipolar Disorders, 2:81-86 (1999).
Hayes, "Acetozolamide in Bipolar Affective Disorders," Annals of Clinical Psychiatry, 6(2):91-98 (1994).
Hu et al., "FGF-18, a Novel Member of the Fibroblast Growth Factor Family, Stimulates Hepatic and Intestinal Proliferation," Molecular and Cellular Biology, 18(10):6063-6074 (Oct. 1998).
Hu et al., "Human Fibroblast Growth Factor-18 Stimulates Fibroblast Cell Proliferation and is Mapped to Chromosome 14p11", Oncogene, 18:2635-2642 (1999).
Impey et al., "Making New Connections: Role of ERK/MAP Kinase Signaling in Neuronal Plasticity", Neuron, 23:11-14 (May 1999).

(56) References Cited

OTHER PUBLICATIONS

Ishii et al., "Protein Kinase C Activation and its Role in the Development of Vascular Complications in Diabetes Mellitus," J. Mol. Med., 76:21-31 (1998).
Katzoff et al., "Nitric Oxide Is Necessary for Multiple Memory Processes after Learning That a Food Is Inedible in Aplysia," The Journal of Neurosciences, 22(21):9581-9594 (Nov. 1, 2002).
Kornhauser et al., "A Kinase to Remember: Dual Roles for MAP Kinase in Long-Term Memory", Neuron, 18:839-842 (Jun. 1997).
Kosik et al., "Microtubule-associated Protein 2: Monoclonal Antibodies Demonstrate the Selective Incorporation of Certain Epitopes into Alzheimer Neurofibrillary Tangles", Proc. Natl. Acad. Sci. USA, 81:7941-7945 (Dec. 1984).
Kravitz et al., "Dietary Supplements of Phenylalanine and Other Amino Acid Precursors of Brain Neuroamines in the Treatment of Depressive Disorders", Journal of the American Osteopathic Associate, 84(1 Suppl):119-123 (Sep. 1984).
Lamberti et al., "Antidepressant-like effects of endogenous histamine and of two histamine H1 receptor agonists in the mouse forced swim test", British Journal of Pharmacology, Nature Publishing Group, Basingstoke, Hants; GB, vol. 123, No. 7, Jan. 1, 1998, pp. 1331-1336.
Lee et al., "Ubiquitination of Protein Kinase C-a and Degradation by the Proteasome," J. Biol. Chem., vol. 271, No. 35, pp. 20973-27976, Jun. 3, 1996.
Lenox et al., "Lithium and the Brain: A Psychopharmacological Strategy to a Molecular Basis for Manic Depressive Illness," Clin. Chem, 40(2):309-314 (1994).
Lyketsos, "Treating Depression in Alzheimer Disease, Efficacy and Safety of Sertraline Therapy, and the Benefits of Depression Reduction: The DIADS", Arch Gen Psychiatry, 2003, 60, pp. 737-746.
Manji et al. "Protein Kinace C Signaling in the Brain: Molecular Transduction of Mood Stabilization in the Treatment of Manic-Depressive Illness," Bioi Psychiatry 46:1328-1351 (1999).
Manji et al., "Post-receptor Signaling Pathways in the Pathophysiology and Treatment of Mood Disorders," Mood Disorders, 481-489, 2000.
Mannisto et al., "Beneficial Effects of Co-administration of Catechol-O-Methyltransferase Inhibitors and L-dihydroxyphenylalanine in Rat Models of Depression", European Journal of Pharmacology, 274:229-233 (1995).
Martin et al., "Role of vitamin E and C on neurodegenerative diseases and cognitive performance," Nutrition Review vol. 60, No. 11, pp. 308-326, 2002.
Masson et al., "Neurotransmitter Transporters in the Central Nervous System," Pharmacological Reviews,51(3):439-464 (1999).
Mody et al., "Genome-wide gene expression profiles of the developing mouse hippocampus,", PNAS, 98(14):8862-8867 (Jul. 17, 2001).
Morishita et al., "Different Effect of Desipramine on Protein Kinase C in Platelets Between Bipolar and Major Depressive Disorders," Psychiatry and Clinical Neurosciences, 53:11-15 (1999).
Morishita et al., "Effects of Tricyclic Antidepressants on Protein Kinase C Activity in Rabbit and Human Platelets in Vivo," Journal of Affective Disorders, 70:329-332 (2002).
Ohbayashi et al., "Structure and Expression of the mRNA Encoding a Novel Fibroblast Growth Factor, FGF-18," The Journal of Biological Chemistry, 273(29):18161-18164 (1998).
Pandey et al., "Protein Kinace C in Platelets of Depressed Patients," Biological Psychiatry, 44:909-911 (1998).
Pandey et al., "Protein Kinase C and Phospholipase C Activity and Expression of Their Specific Isozymes is Decreased and Expression of MARCKS is Increased in Platelets of Bipolar but Not in Unipolar Patients," Neuropschoparmacology, 26(2):216-228 (2002).
Partial European Search Report EP 08 01 0738, dated Oct. 13, 2009.
Partial European Search Report EP 12005992.8, dated Jan. 31, 2013, 8 pages.
Pettit et al., "Antineoplastic Agents 224 Isolation and Structure of Neristatin 1," Journal of the American Chemical Society, 113(17):6693-6695 (1991).
PKC LAB, pp. 1-4, 2010, retrieved from: http://www.pkclab.org/PKC/PKCbiology_PKC_activators.htm.
Popoli et al., "Second Messenger-Regulated Protein Kinases in the Brain: Their Functional Role and the Action of Antidepressant Drugs," J. Neurochem.74(1):21-31 (2000).
Protein Kinase C, pp. 1-6, 2010, retrieved from: http://en.wikipedia.org/wiki/Protein_kinase_C.
Sano et al., "A Controlled Trial of Selegiline, Alpha-Tocopherol, or Both as Treatment For Alzheimer's Disease", New England Journal of Medicine, pp. 1216-1222, Apr. 24, 1997.
Shelton, "Cellular Mechanisms in the Vulnerability to and Depression Response to Antidepressants," Depression, 23(4) (Dec. 2000).
Sun et al., "Carbonic Anhydrase Gating of Attention: Therapy and Enhancement," Trends in Pharmacological Sciences, 23(2) (Feb. 2002), pp. 83-89.
Sun et al., "Depressed or Demented: Common CNS Drug Targets?!", Current Drug Targets—CNS & Neurological Disorders 2002, 1, 575-592 (abstract only).
Sun et al., "Functional Switching of GABAergic Synapses by Ryanodine Receptor Activation," Proc. Nat'l, Acad. Sci USA, 97:12300-12305 (2000).
Sun et al., "Synergistic Effects of Chronic Bryostatin-1 and Alpha-tocopherol on Spatial Learning and Memory," Eur. J. Pharmacol., 584:328-337 (2008).
Supuran et al., "Carbonic Anhydrase Activators. XV. A Kinetic Study of Interaction of Bovine Isozyme II with Pyrazoles, Bis- and Tris-azolyl-methanes," Biol. Pharm. Bull., 19(11):1417-1422 (1988).
Suzuki et al., "Altered 5-HT-Induced Calcium Response in the Presence of Staurosporine in Blood Platelets from Bipolar Disorder Patients," Neuropsychopharmacology, 28:1210-1214 (2003).
Tischmeyer et al., "Activation of Immediate Early Genes and Memory Formation", CMLS, Cell. Mol. Life Sci., 55:564-574 (1999).
Tsien et al., "The Essential Role of Hippocampal CA1 NMDA Receptor-Dependent Synaptic Plasticity in Spatial Memory," Cell, 87:1327-1338 (Dec. 27, 1996).
Wang et al., "Flouxetine Depresses Glutamate Exocytosis in the Rat Cerebrocortical Nerve Terminals (Synaptosomes) via Inhibition of p/a Ca2+ Channels," Synapse, 48:170-177 (2003).
Wang et al., "Increased Membrane-Associated Protein Kinase C Activity and Translocation in Blood Platelets from Bipolar Affective Disorder Patients," Journal of Psychiatric Research, 33:171-179 (1999).
Wender et al., "Function Oriented Synthesis: The Design, Synthesis, PCK Binding and Translocation Activity of a New Bryostatin Analog," 1 Curr. Drug Disc. Tech. 1 (2004).
Wender, "Role of the A-Ring of Bryostatin Analogues in PKkC Binding: Synthesis and Initial Biological Evaluation of New A-Ring Modified," Bryologs. Organic Letters, 7(10):1995-1998 (2005).
Woolf et al., "Hippocampal Microtubule-associated Protein-2 Alterations with Contextual Memory", Brain Research, 821(1):241-249 (Mar. 6, 1999).
Yamanouchi et al., "Early Forms of Microtubule-associated Protein are Strongly Expressed in Cortical Dysplasia", Acta Neuropathol, 95:466-470 (1998).
Yildiz, "Phosphoinositide metabolism, lithium and manic depressive illness," Spectroscopy 16:307-316 (2002).
Zhang et al., "Citron Binds to PSD-95 at Glutamatergic Synapses on Inhibitory Neurons in the Hippocampus," The Journal of Neuroscience, 19(1):96-108 (Jan. 1, 1999).
Zhen et al., "The p38 Mitogen-Activated Protein Kinase Is Involved in Associative Learning in Rabbits," The Journal of Neuroscience, 2(15):5513-5519 (Aug. 1, 2001).

* cited by examiner

PROTEIN SYNTHESIS REQUIRED FOR LONG-TERM MEMORY IS INDUCED BY PKC ACTIVATION ON DAYS PRECEDING ASSOCIATIVE LEARNING

PRIORITY OF INVENTION

This application is a continuation of U.S. application Ser. No. 12/851,222, filed Aug. 5, 2010 now abandoned, which is a continuation of U.S. application Ser. No. 11,494,636, filed Jul. 28, 2006 now abandoned, which claims priority to U.S. Provisional Application No. 60/703,501 filed Jul. 29, 2005 and U.S. Provisional Application No. 60/728,753 filed on Oct. 21, 2005, all of which are incorporated herein by reference.

FIELD OF THE INVENTION

The present invention relates to methods of upregulating and downregulating protein kinase C that are useful for enhancing memory and the treatment of cell proliferative disorders.

BACKGROUND OF THE INVENTION

Various disorders and diseases exist which affect cognition. Cognition can be generally described as including at least three different components: attention, learning, and memory. Each of these components and their respective levels affect the overall level of a subject's cognitive ability. For instance, while Alzheimer's Disease patients suffer from a loss of overall cognition and thus deterioration of each of these characteristics, it is the loss of memory that is most often associated with the disease. In other diseases patients suffer from cognitive impairment that is more predominately associated with different characteristics of cognition. For instance, Attention Deficit Hyperactivity Disorder (ADHD), focuses on the individual's ability to maintain an attentive state. Other conditions include general dementias associated with other neurological diseases, aging, and treatment of conditions that can cause deleterious effects on mental capacity, such as cancer treatments, stroke/ischemia, and mental retardation.

The requirement of protein synthesis for long-term memory has been demonstrated over several decades for a variety of memory paradigms. Agranoff et al. (1967) *Science* 158: 1600-1601; Bergold et al. (1990) *Proc. Natl. Acad. Sci.* 87:3788-3791; Cavallaro et al. (2002) *Proc. Natl. Acad. Sci.* 99: 13279-16284; Crow et al. (1990) *Proc. Natl. Acad. Sci.* 87: 4490-4494; Crow et al. (1999) *J. Neurophysiol.* 82: 495-500; Epstein et al. (2003) *Neurobiol. Learn. Mem.* 79: 127-131; Ezzeddine et al. (2003) *J. Neurosci.* 23: 9585-9594; Farley et al. (1991) *Proc. Natl. Acad. Sci.* 88: 2016-2020; Flexner et al. (1996) *Proc. Natl. Acad. Sci.* 55: 369-374; Hyden et al. (1970) *Proc. Natl. Acad. Sci.* 65: 898-904; Nelson et al. (1990) *Proc. Natl. Acad. Sci.* 87: 269-273; Quattrone et al. (2001) *Proc. Natl. Acad. Sci.* 98: 11668-11673; Zhao et al. (1999) *J. Biol. Chem.* 274: 34893-34902; Zhao et al. (2000) *FASEB J.* 14: 290-300. Flexner originally showed that drug-induced inhibition of protein synthesis (e.g., with 5-propyluracil or anisomycin) blocked long-term memory when this inhibition occurred during a critical time interval following the training paradigm. Flexner et al. (1996) *Proc. Natl. Acad. Sci.* 55: 369-374. If protein synthesis was inhibited before this critical time window or at any time after this window, there was no effect on long-term memory. The identity of the proteins essential for memory consolidation, the mechanisms of their regulation, and their role in the consolidation of long-term memory has remained a mystery.

In many species the formation of long-term associative memory has also been shown to depend on translocation, and thus activation, of protein kinase C (PKC) isozymes to neuronal membranes. Initially, these PKC isozymes, when activated by a combination of calcium and co-factors, such as diacylglycerol, achieve a stable association with the inner aspect of the external neuronal membrane and membranes of internal organelle, such as the endoplasmic reticulum. PKC activation has been shown to occur in single identified Type B cells of the mollusk *Hermissenda* (McPhie et al. (1993) *J. Neurochem.* 60: 646-651), a variety of mammalian associative learning protocols, including rabbit nictitating membrane conditioning (Bank et al. (1988) *Proc. Natl. Acad. Sci.* 85: 1988-1992; Olds et al. (1989) *Science* 245: 866-869), rat spatial maze learning (Olds et al. (1990) *J. Neurosci.* 10: 3707-3713), and rat olfactory discrimination learning, upon Pavlovian conditioning. Furthermore, calexcitin (Nelson et al. (1990) *Science* 247: 1479-1483), a high-affinity substrate of the alpha isozyme of PKC increased in amount and phosphorylation (Kuzirian et al. (2001) *J. Neurocytol.* 30: 993-1008) within single identified Type B cells in a Pavlovian-conditioning-dependent manner.

There is increasing evidence that the individual PKC isozymes play different, sometimes opposing, roles in biological processes, providing two directions for pharmacological exploitation. One is the design of specific (preferably, isozyme specific) inhibitors of PKC. This approach is complicated by the fact that the catalytic domain is not the domain primarily responsible for the isotype specificity of PKC. The other approach is to develop isozyme-selective, regulatory site-directed PKC activators. These may provide a way to override the effect of other signal transduction pathways with opposite biological effects. Alternatively, by inducing downregulation of PKC after acute activation, PKC activators may cause long term antagonism.

Following associative memory protocols, increased PKC association with the membrane fractions in specific brain regions can persist for many days (Olds et al. (1989) *Science* 245: 866-869). Consistent with these findings, administration of the potent PKC activator bryostatin, enhanced rats spatial maze learning (Sun et al. (2005) *Eur. J. Pharmacol.* 512: 45-51). Furthermore, clinical trials with the PKC activator, bryostatin, suggested (Marshall et al. (2002) *Cancer Biology & Therapy* 1: 409-416) that PKC activation effects might be enhanced by an intermittent schedule of drug delivery. One PKC activator, bryostatin, a macrolide lactone, activates PKC in sub-nanomolar concentrations (Talk et al. (1999) *Neurobiol. Learn. Mem.* 72: 95-117). Like phorbol esters and the endogenous activator DAG, bryostatin binds to the C1 domain within PKC and causes its translocation to membranes, which is then followed by downregulation.

The non-tumorigenic PKC activator, bryostatin, has undergone extensive testing in humans for the treatment of cancer in doses (25 $\mu g/m^2$-120 $\mu g/m^2$) known to cause initial PKC activation followed by prolonged downregulation (Prevostel et al. (2000) *Journal of Cell Science* 113: 2575-2584; Lu et al. (1998) *Mol. Biol. Cell* 18: 839-845; Leontieva et al. (2004) *J. Biol. Chem.* 279:5788-5801). Bryostatin activation of PKC has also recently been shown to activate the alpha-secretase that cleaves the amyloid precursor protein (APP) to generate the non-toxic fragments soluble precursor protein (sAPP) from human fibroblasts (Etcheberrigaray et al. (2004) *Proc. Natl. Acad. Sci.* 101: 11141-11146). Bryostatin also enhances learning and memory retention of the rat spatial maze task (Sun et al. (2005) *Eur. J. Pharmacol.* 512: 45-51), learning of the rabbit nictitating membrane paradigm (Schreurs and Alkon, unpublished), and in a preliminary report, *Hermissenda* conditioning (Scioletti et al. (2004) *Biol. Bull.* 207: 159). Accordingly, optimal activation of PKC is important for many molecular mechanisms that effect cognition in normal and diseased states.

Because the upregulation of PKC is difficult to achieve without downregulation, and vice versa, methods of upregulation of PKC while minimizing downregulation are needed to enhance the cognitive benefits observed associated with PKC activation. The methods and compositions of the present invention fulfill these needs and will greatly improve the clinical treatment for Alzheimer's disease and other neurodegenerative diseases, as well as, provide for improved cognitive enhancement prophylactically. The methods and compositions also provide treatment and/or enhancement of the cognitive state through the modulation of α-secretase.

SUMMARY OF THE INVENTION

This invention relates to a method of contacting a PKC activator with protein kinase C in a manner sufficient to stimulate the synthesis of proteins sufficient to consolidate long term memory.

In one embodiment, the PKC activator is a macrocyclic lactone. In one embodiment, the PKC activator is a benzolactam. In one embodiment, the PKC activator is a pyrrolidinone. In a preferred embodiment, the macrocyclic lactone is bryostatin. In a more preferred embodiment, the bryostatin is bryostatin-1, -2, -3, -4, -5, -6, -7, -8, -9, -10, -11, -12, -13, -14, -15, -16, -17, or -18. In the most preferred embodiment, the bryostatin is bryostatin-1.

In one embodiment, the macrocyclic lactone is neristatin. In a preferred embodiment, the neristatin is neristatin-1.

In one embodiment, the contact activates PKC. In one embodiment, the contact increases the amount of PKC. In one embodiment, the contact increases the synthesis of PKC. In one embodiment, the contact increases the amount of calexcitin. In one embodiment, the contact does not result in substantial subsequent deregulation of PKC.

In one embodiment, the contact is repeated. In another embodiment, the contact is repeated at regular intervals. In another embodiment, the interval is between one week to one month, one day and one week, or less than one hour and 24 hours. In another embodiment, the interval is between one week and one month. In another embodiment, the interval is between one day and one week. In another embodiment, the interval is between less than one hour and 24 hours.

In one embodiment, the contact is maintained for a fixed duration. In another embodiment, the fixed duration is less than 24 hours. In another embodiment, the fixed duration is less than 12 hours. In another embodiment, the fixed duration is less than 6 hours. In another embodiment, the fixed duration is less than 6 hours. In another embodiment, the fixed duration is less than 4 hours. In another embodiment, the fixed duration is less than 2 hours. In a preferred embodiment, the fixed duration is between about 1 and 12 hours. In a more preferred embodiment, the fixed duration is between about 2 and 6 hours. In the most preferred embodiment, the fixed duration is about 4 hours.

In one embodiment, the contact is repeated for a period greater than one day. In another embodiment, the contact is repeated for a period between one day and one month. In another embodiment, the contact is repeated for a period between one day and one week. In another embodiment, the contact is repeated for a period between one week and one month. In another embodiment, the contact is repeated for a period between one month and six months. In another embodiment, the contact is repeated for a period of one month. In another embodiment, the contact is repeated for a period greater than one month.

The invention relates to a method of contacting a PKC activator with protein kinase C in a manner sufficient to downregulate PKC.

In one embodiment, the PKC activator is a macrocyclic lactone. In one embodiment, the PKC activator is a benzolactam. In one embodiment, the PKC activator is a pyrrolidinone. In a preferred embodiment, the macrocyclic lactone is bryostatin. In a more preferred embodiment, the bryostatin is bryostatin-1, -2, -3, -4, -5, -6, -7, -8, -9, -10, -11, -12, -13, -14, -15, -16, -17, or -18. In the most preferred embodiment, the bryostatin is bryostatin-1.

In one embodiment, the macrocyclic lactone is neristatin. In a preferred embodiment, the neristatin is neristatin-1.

In one embodiment, the contact does not stimulate the synthesis of PKC. In another embodiment, the contact does not substantially stimulate the synthesis of PKC. In another embodiment, the contact decreases the amount of PKC. In another embodiment, the contact substantially decreases the amount of PKC. In another embodiment, the contact does not stimulate the synthesis of calexcitin.

In one embodiment, the contact is for a sustained period. In one embodiment, the sustained period if between less than one hour and 24 hours. In another embodiment, the sustained period is between one day and one week. In another embodiment, the sustained period is between one week and one month. In another embodiment, the sustained period is between less than one hour and 12 hours. In another embodiment, the sustained period is between less than one hour and 8 hours. In another embodiment, the sustained period is between less than one hour and 4 hours. In a preferred embodiment, the sustained period is about 4 hours.

In one embodiment, the contact produces sustained downregulation of PKC.

This invention relates to a method of contacting a PKC activator with protein kinase C in a manner sufficient to stimulate the synthesis of proteins sufficient to consolidate long term memory, further comprising the step of inhibiting degradation of PKC.

In one embodiment, the degradation is through ubiquitination. In another embodiment, the degradation is inhibited by lactacysteine. In another embodiment, the PKC is human.

This invention relates to a method of contacting a PKC activator with protein kinase C in a manner sufficient to stimulate the synthesis of proteins sufficient to consolidate long term memory, wherein the PKC activator is provided in the form of a pharmaceutical composition comprising the PKC activator and a pharmaceutically acceptable carrier.

In one embodiment, the pharmaceutical composition further comprises a PKC inhibitor. In another embodiment, the PKC inhibitor is a compound that inhibits PKC in peripheral tissues. As used herein, "peripheral tissues" means tissues other than brain. In another embodiment, the PKC inhibitor is a compound that preferentially inhibits PKC in peripheral tissues. In another embodiment, the PKC inhibit is a compound that reduces myalgia associated with the administration of a PKC activator to subjects in need thereof. In another embodiment, the PKC inhibitor is a compound that reduces myalgia produced in a subject treated with a PKC activator. In another embodiment, the PKC inhibitor is a compound that increases the tolerable dose of a PKC activator. Specifically, PKC inhibitors include, for example, but are not limited to vitamin E, vitamin E analogs, and salts thereof; calphostin C; thiazolidinediones; ruboxistaurin, and combinations thereof.

As used herein, "vitamin E" means α-tocopherol (5,7,8-trimethyltocol); β-tocopherol (5,8-dimethyltocol); δ-tocopherol (8-methyltocal); and γ-tocopherol (7,8-dimethyltocol), salts and analogs thereof.

Figure (C) displays intensity measures for *Hermissenda* conditioned with 9-random TEs (left bar) and animals treated with two exposures on successive days to the PKC antagonist, bryostatin (0.25 ng/ml), and then associatively conditioned with 2-paired TEs. Activation of PKC from two exposures of bryostatin coupled with 2TEs significantly increased calexcitin to levels associated with 9-paired TEs and consolidated (long-term) memory (n=4-8 animals/condition/replicate; t-test comparison, $p<0.01$).

Calexcitin immunostaining is sufficiently sensitive to resolve boutons within synaptic of photic-vestibular neurites (D). Arrows indicate arborization field between an interneuron (a), axon from a contralateral neuron (b), and terminal boutons of neurites from a putative photoreceptor (c). Scale bars=10 μm; CPG, cerebropleural ganglion.

Figure 10A:
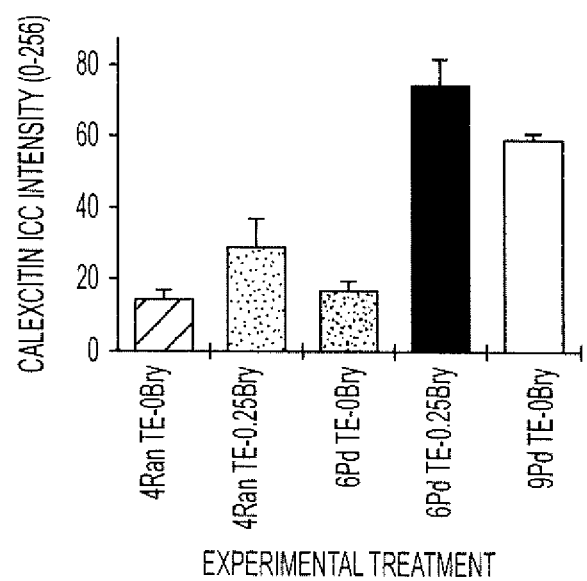

FIG. 10a depicts the effect of bryostatin and training events on calexcitin immunostaining. The figure shows calexcitin increased within Type B cells with the number of training events. Immuno-intensity measurements (as grey-scale intensity; 0-256) of calexcitin (CE) antibody labeling as a function of bryostatin and training regime. Randon training (4-TEs) without bryostatin yielded slightly higher intensity measures than background. Bryostatin administration increased the calexcitin levels fro both training paradigms. With random training, when there was occasional overlap (pairing) of the CS and US, as was the case here, it is not unexpected that some rise in CE might occur (increase of 2.0). However, calexcitin levels increased greater than 4.3× with paired training (mean±SE, N=5 animals/treatment. 4RTE=random control, 4 trials with random light and rotation; 6PTE=paired trials, 6 trials with paired light and rotation. (6PTE-0Bry vs. 6PTE-0.25Bry; $p<0.001$; 4RTE-0.25Bry vs. 6PTE-0.25 Bry; $p<0.001$ (t-test).

Figure 10B:
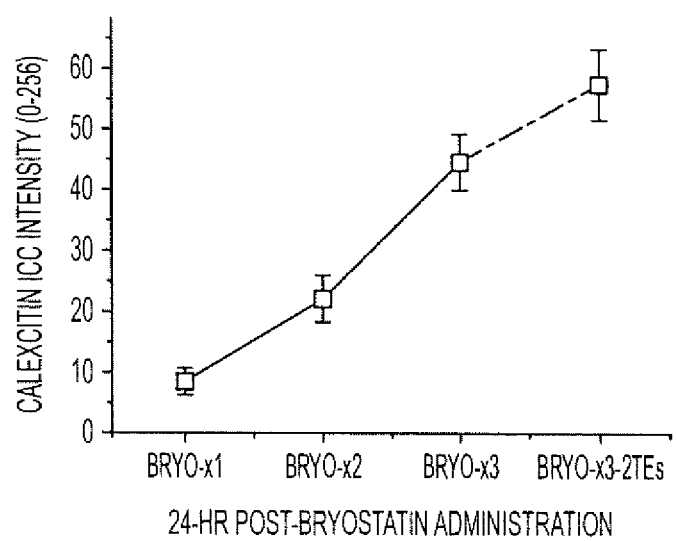

FIG. 10b depicts the effect of bryostatin alone calexcitin, as shown by immunostaining. Bryostatin alone (without associative conditioning) administered for 4-hr over each of 1, 2, and 3 days progressively increased the levels of calexcitin in the B-photoreceptors of *Hermissenda* when measured 24 hours after each of the periods of bryostatin exposures. The calexcitin level after 3 bryostatin exposures followed by just 2-paired training events (paired light and orbital shaking) raised that level even higher with a significant concomitant length in the number of retention days for the associative conditioning-induced behavioral modification (n=16 animals/condition: ANOVA, $p<0.01$).

Figure 11A:
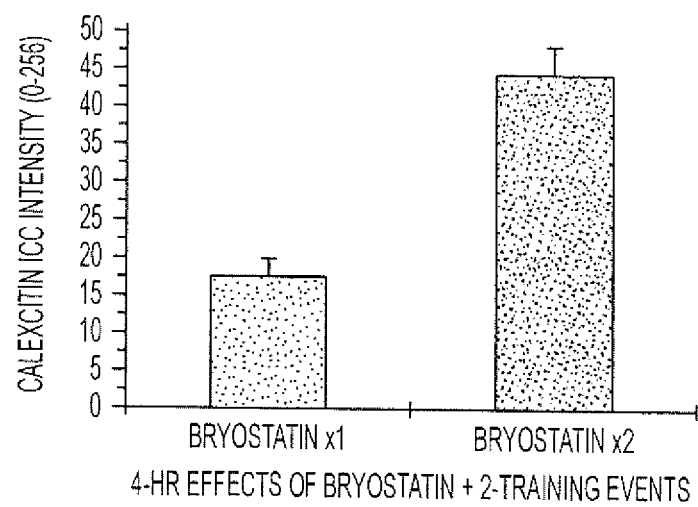

FIG. 11a depicts the effect of 4-hour bryostatin exposure, on two consecutive days, followed 24 hours later by two training events, on the intensity of calexcitin. The figure shows that exposure to 4 hours of bryostatin on two consecutive days followed 24 hours later by 2 TEs are required to raise calexcitin levels to the amount associated with consolidated long-term memory. Exposure to 4-hr of bryostatin on two consecutive days followed 24 hours later by 2-training events (2TE) are required to raise calexcitin levels to the amount associated with consolidated long-term memory, Typically, 2-TEs with two bryostatin exposures produces retention lasting more than one week (n=16 animals/condition; t-test, $p<0.01$).

Figure 11B:
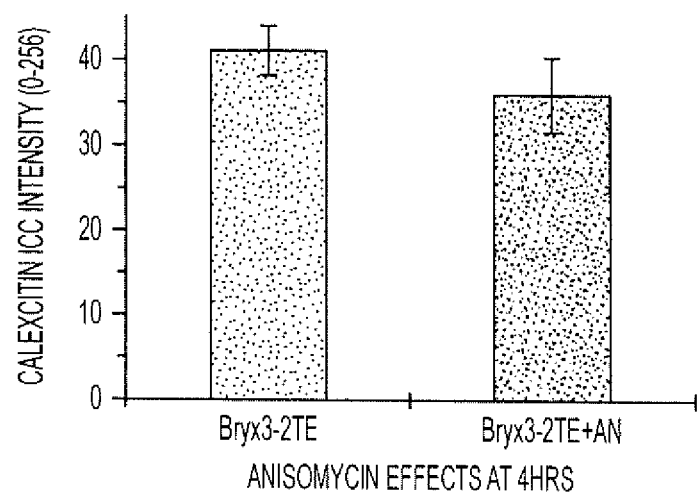

FIG. 11b depicts the effect of adding anisomycin after bryostatin exposure on calexcitin. The figure shows that anisomycin following 2 TE plus 3 days of 4 hour bryostatin exposures did not reduce the calexcitin immunostaining. Priming with 4-hr exposures to bryostatin over 3 consecutive days will induce calexcitin levels required for consolidated memory. Anisomycin added immediately after the 2-paired training events did not reduce this calexcitin level and consolidated memory persists for many days (N=8 animals/condition; t-test, $p>0.05$, ns).

Figure 12:
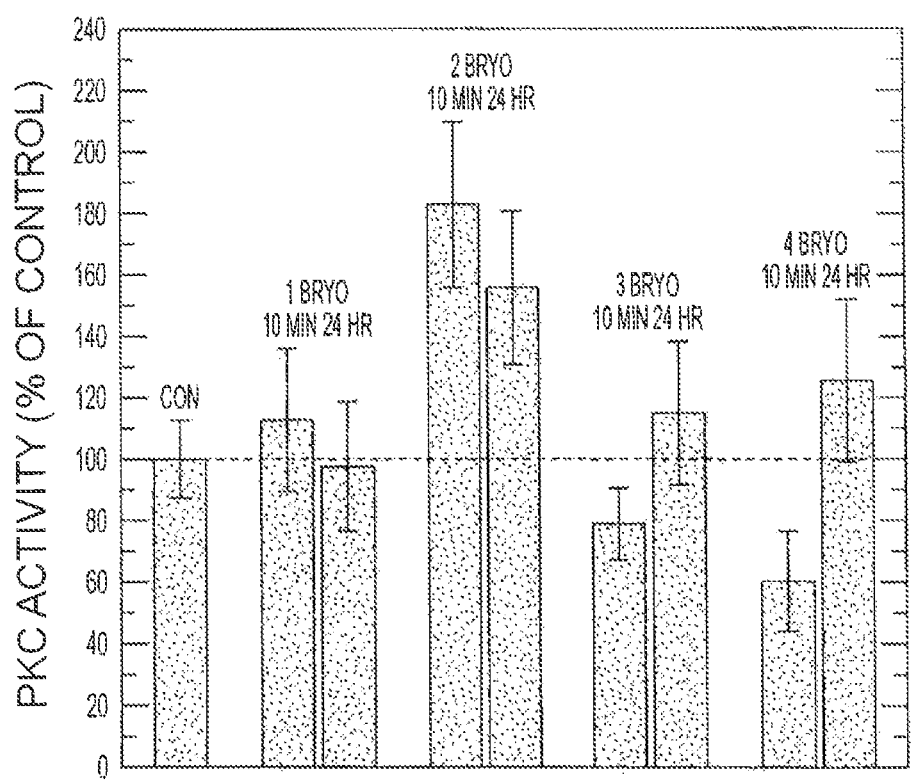

FIG. 12 depicts the effects of repeated 4-hour bryostatin exposure on PKC activity, as measured by histone phosphorylation in the cytosolic fraction. The figure shows bryostatin exposure on two successive produces PKC activity significantly above control or baseline levels. PKC activity in *Hermissenda* nervous systems (cytosol) after bryostatin. Intact *Hermissenda* were exposed for 4 hour intervals to bryostatin (0.28 nM) on successive days under conditions described ("Behavioral Pharmacology"). Histone phosphorylation (See "Methods") in isolated circumesophageal nervous systems was then measured in the cytosol fraction. PKC activity measured both 10 minutes and 24 hours after the second of two bryostatin exposures was significantly increased over baseline levels (N=6, for each measurement).

Figure 13:
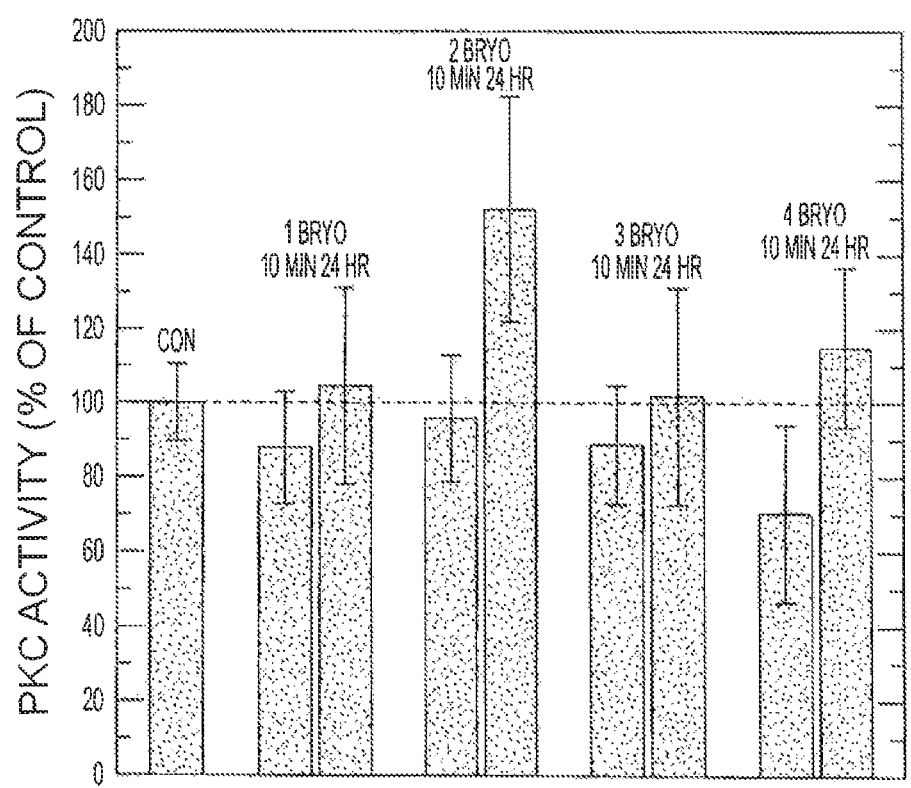

FIG. 13 depicts the effects of repeated 4-hour bryostatin exposure on PKC activity, as measured by histone phosphorylation in the membrane fraction. The figure shows bryostatin exposure on two successive produces PKC activity significantly above control or baseline levels. PKC activity in *Hermissenda* nervous systems (membrane) after bryostatin. As in FIG. 12, histone phosphorylation was measured in the membrane fraction. PKC activity measured 24 hours after the second of two bryostatin exposures was significantly increased over baseline (N=6) for each measurement.

Figure 14:
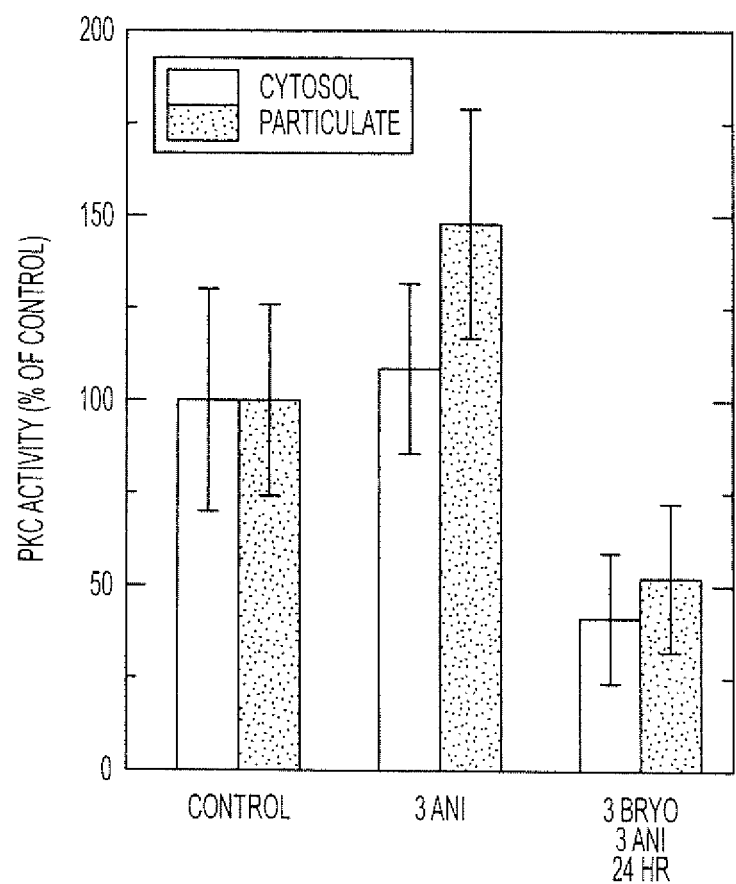

FIG. 14 depicts the effects of anisomycin on PKC activity. The figure shows that the presence of anisomycin during each of three successive days of bryostatin exposure reduced PKC activity in both cytosolic and membrane fractions. Anisomycin reduces PKC activity in *Hermissenda*. As in FIG. 12, 13 but with anisomycin (1.0 ng/ml) added together with each bryostatin (0.25 ng/ml) exposure. Note that the anisomycin markedly reduced the PKC activity in both the cytosolic and membrane fractions from the *Hermissenda* circumesophagel nervous systems after exposure to bryostatin on three successive days (N=3, for each measurement, $p<0.01$).

Figure 15:
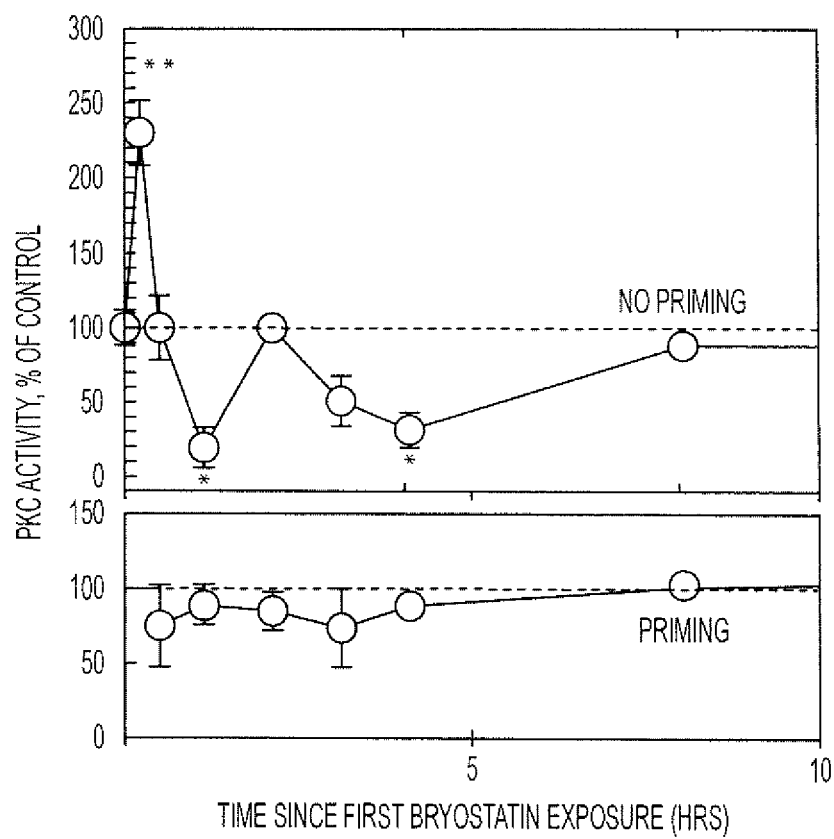

FIG. 15 depicts the effects of bryostatin on membrane-bound PKC in hippocampal neurons. The figure shows that exposure of cultured hippocampal neurons to a single activating dose of bryostatin (0.28 nM) for 30 minutes produced a brief translocation of PKC from the cytosol to the particulate fraction (approx 60%) followed by a prolonged downregulation. A second exposure of up to four hours after the first exposure significantly attenuates the down regulation found four hours after a single bryostatin exposure. Effect of bryostatin on membrane-bound PKC activity in hippocampal cultured IGF/IR cells after 1) a single 30 min exposure; or 2) two 30 min exposures separated by intervals of 30 min to 8 hr. A second exposure up to 4 hr after the first exposure significantly attenuates the downregulation found 4 hr after a single bryostatin exposure (N=6 for each measurement, $*p<0.05$, $**p<0.01$).

Figure 16:
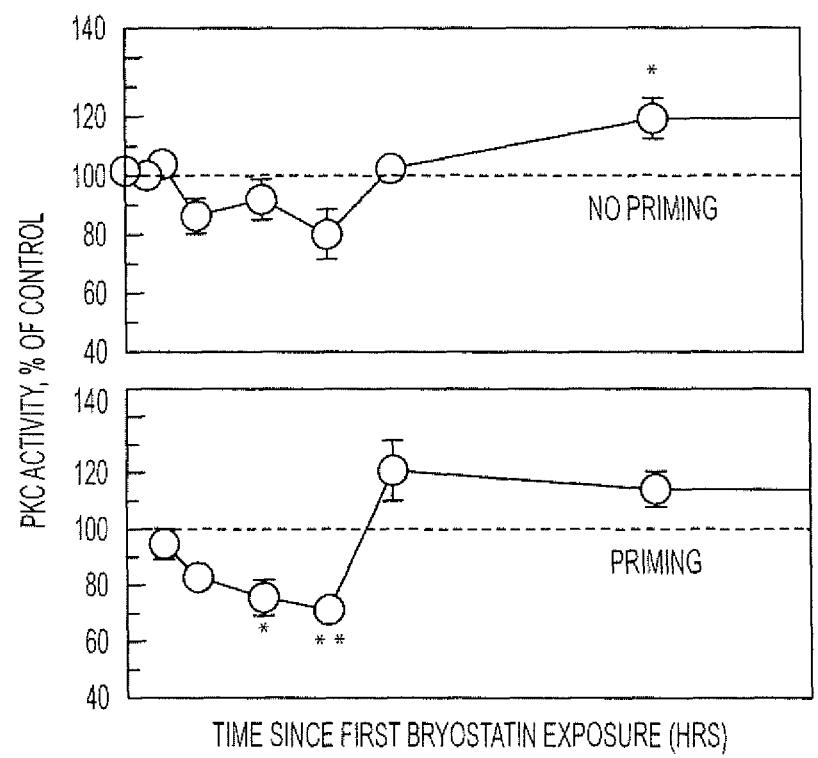

FIG. 16 depicts the effects of repeated bryostatin exposure on PKC activity. The figure shows that a second exposure after a 2- to 4-hour delay eliminated the significant downregulation that a single 30-minute bryostatin exposure produced, and that if the second exposure was delayed until 4 hours after the first, activity was increased above baseline, to a degree that was significantly greater compared with a second exposure delivered after 2 hours or less. Effect of bryostatin on cytosolic PKC activity in hippocampal cultured IGF/IR cells after 1) a single 30 min exposure, or 2) two 30 min exposures separated by intervals of 30 min to 8 hr. PKC activity was not altered in the cytosol the first 4 hours after bryostatin exposure. By contrast, a second exposure to bryostatin within 2 hr of the first induced a significant reduction of PKC activity. However, if the second exposure was delayed until 4 hours after the first, activity was increased above baseline, and was significantly greater than activity measure in response to a second exposure delivered after 1 or 2 hours (N=6 for each measurement, *p<0.05, **p<0.01).

Figure 17A:
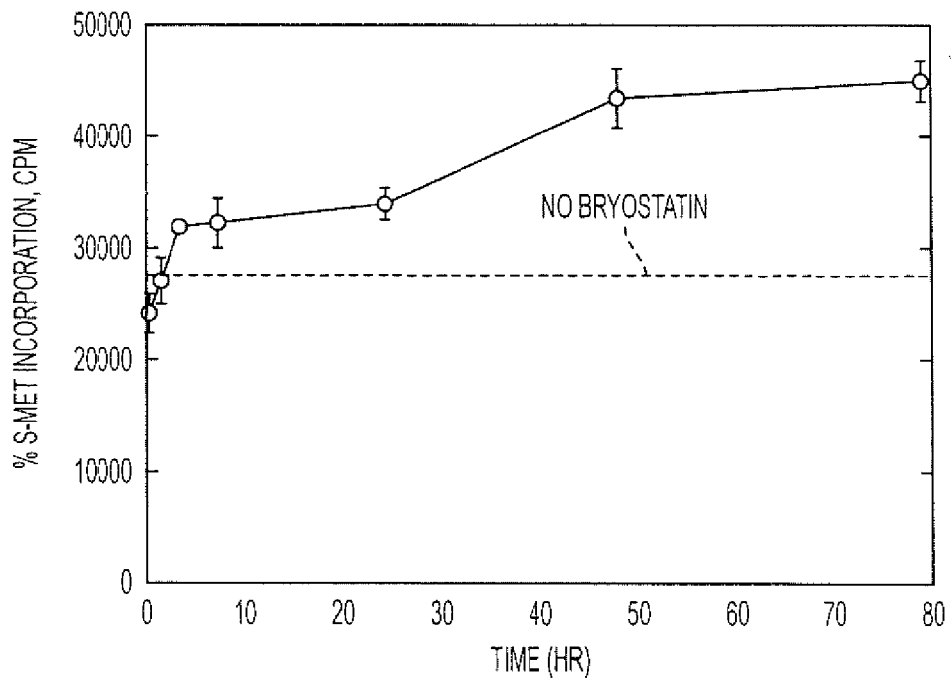
Figure 17B:
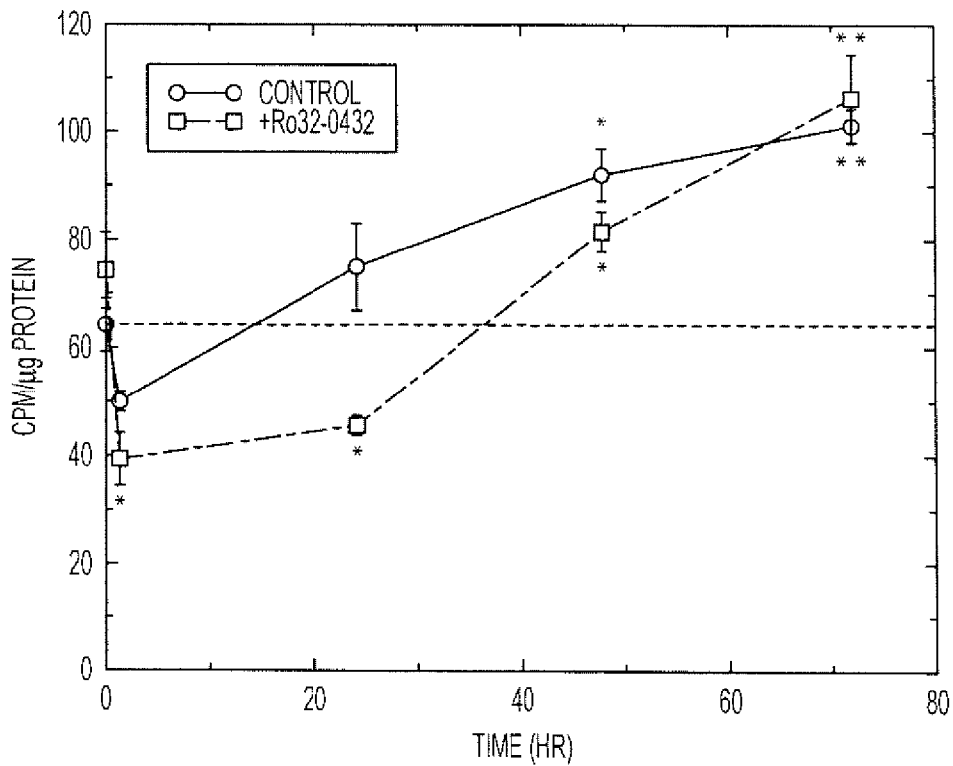

FIG. 17 depicts the effects of bryostatin on protein synthesis. Rat IGF-IR cells were incubated for 30 minutes with 0.28 nM bryostatin for incubation times ranging from 1 to 79 hours. [$^{35}$S]Methionine (9.1 µCi) was then added to the medium followed by analysis of radiolabel. A single 30-minute exposure to 0.28 nM bryostatin increased overall protein synthesis, as measured by the incorporation of [$^{35}$S] Methionine in the last half hour before collecting the neurons, by 20% within 24 hours, increasing to 60% by 79 hours after bryostatin exposure, but increasing significantly less in the presence of the PKC inhibitor Ro-32-0432.

DETAILED DESCRIPTION OF THE INVENTION

1. Definitions

As used herein, "upregulating" or "upregulation" means increasing the amount or activity of an agent, such as PKC protein or transcript, relative to a baseline state, through any mechanism including, but not limited to increased transcription, translation and/or increased stability of the transcript or protein product.

As used herein, "down regulating" or "down regulation" means decreasing the amount or activity of an agent, such as PKC protein or transcript, relative to a baseline state, through any mechanism including, but not limited to decreased transcription, translation and/or decreased stability of the transcript or protein product.

As used herein, the term "pharmaceutically acceptable carrier" means a chemical composition, compound, or solvent with which an active ingredient may be combined and which, following the combination, can be used to administer the active ingredient to a subject. As used herein, "pharmaceutically acceptable carrier" includes, but is not limited to, one or more of the following: excipients; surface active agents; dispersing agents; inert diluents; granulating and disintegrating agents; binding agents; lubricating agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; antioxidants; stabilizing agents; and pharmaceutically acceptable polymeric or hydrophobic materials and other ingredients known in the art and described, for example in Genaro, ed. (1985) *Remington's Pharmaceutical Sciences* Mack Publishing Co., Easton, Pa., which is incorporated herein by reference.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

2. Alzheimer's Disease

Alzheimer's disease is associated with extensive loss of specific neuronal subpopulations in the brain with memory loss being the most universal symptom. (Katzman (1986) *New England Journal of Medicine* 314: 964). Alzheimer's disease is well characterized with regard to neuropathological changes. However, abnormalities have been reported in peripheral tissue supporting the possibility that Alzheimer's disease is a systematic disorder with pathology of the central nervous system being the most prominent. (Connolly (1998) *Review, TIPS Col.* 19: 171-77). For a discussion of Alzheimer's disease links to a genetic origin and chromosomes 1, 14, and 21 see St. George-Hyslop et al. (1987) *Science* 235: 885; Tanzi et al. *Review, Neurobiology of Disease* 3:159-168; Hardy (1996) *Acta Neurol Scand: Supplement* 165: 13-17.

Individuals with Alzheimer's disease are characterized by progressive memory impairments, loss of language and visuospatial skills and behavior deficits (McKhann et al. (1986) *Neurology* 34: 939-944). The cognitive impairment of individuals with Alzheimer's disease is the result of degeneration of neuronal cells located in the cerebral cortex, hippocampus, basal forebrain and other brain regions. Histologic analyzes of Alzheimer's disease brains obtained at autopsy demonstrated the presence of neurofibrillary tangles (NFT) in perikarya and axons of degenerating neurons, extracellular neuritic (senile) plaques, and amyloid plaques inside and around some blood vessels of affected brain regions. Neurofibrillary tangles are abnormal filamentous structures containing fibers (about 10 nm in diameter) that are paired in a helical fashion, therefore also called paired helical filaments. Neuritic plaques are located at degenerating nerve terminals (both axonal and dendritic), and contain a core compound of amyloid protein fibers. In summary, Alzheimer's disease is characterized by certain neuropathological features including intracellular neurofibrillary tangles, primarily composed of cytoskeletal proteins, and extracellular parenchymal and cerebrosvascular amyloid. Further, there are now methods in the art of distinguishing between Alzheimer's patents, normal aged people, and people suffering from other neurodegenerative diseases, such as Parkinson's, Huntington's chorea, Wernicke-Korsakoff or schizophrenia further described for instance in U.S. Pat. No. 5,580,748 and U.S. Pat. No. 6,080,582.

While cellular changes leading to neuronal loss and the underlying etiology of the disease remain under investigation the importance of APP metabolism is well established. The two proteins most consistently identified in the brains of patients with Alzheimer's disease to play a role in the physiology or pathophysiology of brain are β-amyloid and tau. (See Selkoe (2001) *Physiological Reviews.* 81:2). A discussion of the defects in β-amyloid protein metabolism and abnormal calcium homeostasis and/or calcium activated kinases. (Etcheberrigaray et al. *Alzheimer's Reports* Vol. Nos. 3, 5 & 6 pp 305-312; Webb et al. (2000) *British Journal of Pharmacology* 130: 1433-52).

Alzheimer's disease (AD) is a brain disorder characterized by altered protein catabolism. Altered protein phosphorylation has been implicated in the formation of the intracellular neurofibrillary tangles found in Alzheimer's disease. The processing of the amyloid precursor protein (APP) determines the production of fragments that later aggregate forming the amyloid deposits characteristic of Alzheimer's disease (AD), known as senile or AD plaques. A central feature of the pathology of Alzheimer's disease is the deposition of amyloid protein within plaques. Thus, APP processing is an early and key pathophysiological event in AD.

Three alternative APP processing pathways have been identified. The previously termed "normal" processing involves the participation of an enzyme that cleaves APP within the Aβ sequence at residue Lys16 (or between Lys16 and Leu17; APP770 nomenclature), resulting in non-amyloidogenic fragments: a large N-terminus ectodomain and a small 9 kDa membrane bound fragment. This enzyme, yet to be fully identified, is known as α-secretase. Two additional secretases participate in APP processing. One alternative pathway involves the cleavage of APP outside the Aβ domain, between Met671 and Asp672 (by β-secretase) and the participation of the endosomal-lysomal system. An additional cleavage site occurs at the carboxyl-terminal end of the Aβ portion, within the plasma membrane after amino acid 39 of the Aβ peptide. The secretase (γ) action produces an extracellular amino acid terminal that contains the entire Aβ sequence and a cell-associated fragment of ~6 kDa. Thus, processing by β and γ secretases generate potential amyloidogenic fragments since they contain the complete Aβ sequence. Several lines of evidence have shown that all alternative pathways occur in a given system and that soluble Aβ may be a "normal product." However, there is also evidence that the amount of circulating Aβ in CSF and plasma is elevated in patients carrying the "Swedish" mutation. Moreover, cultured cells transfected with this mutation or the $APP_{717}$ mutation, secrete larger amounts of Aβ. More recently, carriers of other APP mutations and PS1 and PS2 mutations have been shown to secrete elevated amounts of a particular form, long (42-43 amino acids) Aβ.

Therefore, although all alternative pathways may occur normally, an imbalance favoring amyloidogenic processing occurs in familial and perhaps sporadic AD. These enhanced amyloidogenic pathways ultimately lead to fibril and plaque formation in the brains of AD patients. Thus, intervention to favor the non-amyloidogenic, α-secretase pathway effectively shifts the balance of APP processing towards a presumably non-pathogenic process that increases the relative amount of sAPP compared with the potentially toxic Aβ peptides.

The PKC isoenzymes provides a critical, specific and rate limiting molecular target through which a unique correlation of biochemical, biophysical, and behavioral efficacy can be demonstrated and applied to subjects to improve cognitive ability.

Further with regard to normal and abnormal memory both $K^+$ and $Ca^{2+}$ channels have been demonstrated to play key roles in memory storage and recall. For instance, potassium channels have been found to change during memory storage. (Etcheberrigaray et al. (1992) *Proc. Natl. Acad. Sci.* 89: 7184; Sanchez-Andres et al. (1991) *Journal of Neurobiology* 65: 796; Collin et al. (1988) *Biophysics Journal* 55: 955; Alkon et al. (1985) *Behavioral and Neural Biology* 44: 278; Alkon (1984) *Science* 226: 1037). This observation, coupled with the almost universal symptom of memory loss in Alzheimer's patents, led to the investigation of potassium channel function as a possible site of Alzheimer's disease pathology and the effect of PKC modulation on cognition.

3. Protein Kinase C and Alzheimer's Disease

PKC was identified as one of the largest gene families of non-receptor serine-threonine protein kinases. Since the discovery of PKC in the early eighties by Nishizuka and coworkers (Kikkawa et al. (1982) *J. Biol. Chem.* 257: 13341), and its identification as a major receptor of phorbol esters (Ashendel et al. (1983) *Cancer Res.*, 43: 4333), a multitude of physiological signaling mechanisms have been ascribed to this enzyme. The intense interest in PKC stems from its unique ability to be activated in vitro by calcium and diacylglycerol (and its phorbol ester mimetics), an effector whose formation is coupled to phospholipid turnover by the action of growth and differentiation factors.

The PKC gene family consists presently of 11 genes which are divided into four subgrounds: 1) classical PKCα, $β_1$, $β_2$ ($β_1$ and $β_2$ are alternatively spliced forms of the same gene) and γ, 2) novel PKCδ, ε, η and θ, 3) atypical PKCζ, λ, η and ι and 4) PKCμ. PKCμ resembles the novel PKC isoforms but differs by having a putative transmembrane domain (reviewed by Blohe et al. (1994) *Cancer Metast. Rev.* 13: 411; Ilug et al. (1993) *Biochem J.* 291: 329; Kikkawa et al. (1989) *Ann. Rev. Biochem.* 58: 31). The α, $β_1$, $β_2$, and γ isoforms are $Ca^2$, phospholipid and diacylglycerol-dependent and represent the classical isoforms of PKC, whereas the other isoforms are activated by phospholipid and diacylglycerol but are not dependent on $CA^{2+}$. All isoforms encompass 5 variable (V1-V5) regions, and the α, $β_1$, $β_2$, and γ isoforms are $Ca^2$, (C1-C4) structural domains which are highly conserved. All isoforms except PKCα, β and γ lack the C2 domain, and the λ, η and isoforms also lack nine of two cysteine-rich zinc finger domains in C1 to which diacylglycerol binds. The C1 domain also contains the pseudo substrate sequence which is highly conserved among all isoforms, and which serves an auto regulatory function by blocking the substrate-binding site to produce an inactive conformation of the enzyme (House et al., (1987) *Science* 238: 1726).

Because of these structural features, diverse PKC isoforms are thought to have highly specialized roles in signal transduction in response to physiological stimuli (Nishizuka (1989) *Cancer* 10: 1892), as well as in neoplastic transformation and differentiation (Glazer (1994) *Protein Kinase C*. J. F. Kuo, ed., Oxford U. Press (1994) at pages 171-198). For a discussion of known PKC modulators see PCT/US97/08141, U.S. Pat. Nos. 5,652,232; 6,043,270; 6,080,784; 5,891,906; 5,962,498; 5,955,501; 5,891,870 and 5,962,504.

In view of the central role that PKC plays in signal transduction, PKC has proven to be an exciting target for the modulation of APP processing. It is well established that PKC plays a role in APP processing. Phorbol esters for instance have been shown to significantly increase the relative amount of non-amyloidogenic soluble APP (sAPP) secreted through PKC activation. Activation of PKC by phorbol ester does not appear to result in a direct phosphorylation of the APP molecule, however. Irrespective of the precise site of action, phorbol-induced PKC activation results in an enhanced or favored α-secretase, non-amyloidogenic pathway. Therefore PKC activation is an attractive approach for influencing the production of non-deleterious sAPP and even producing beneficial sAPP and at the same time reduce the relative amount of Aβ peptides. Phorbol esters, however, are not suitable compounds for eventual drug development because of their tumor promotion activity. (Ibarreta et al. (1999) *NeuroReport* Vol. 10, No. 5&6, pp 1034-40).

The present inventors have also observed that activation of protein kinase C favors the α-secretase processing of the Alzheimer's disease (AD) amyloid precursor protein (APP), resulting in the generation of non-amyloidogenic soluble APP (sAPP). Consequently, the relative secretion of amyloidogenic $A_{1-40}$ and $A_{1-42(3)}$ is reduced. This is particularly relevant since fibroblasts and other cells expressing APP and presenilin AD mutations secrete increased amounts of total Aβ and/or increased ratios of $A_{1-42\,(3)}/A_{1-40}$. Interesting, PKC defects have been found in AD brain (α and β isoforms) and in fibroblasts (α-isoform) from AD patients.

Studies have shown that other PKC activators (i.e. benzolactam) with improved selectivity for the α, β and γ isoforms enhance sAPP secretion over basal levels. The sAPP secretion in benzolactam-treated AD cells was also slightly higher compared to control benzolactam-treated fibroblasts, which only showed significant increases of sAPP secretion after treatment with 10 μM BL. It was further reported that staurosporine (a PKC inhibitor) eliminated the effects of benzolactam in both control and AD fibroblasts while related compounds also cause a ~3-fold sAPP secretion in PC12 cells. The present inventors have found that the use of bryostatin as a PKC activators to favor non-amyloidogenic APP processing is of particular therapeutic value since it is non-tumor promoting and already in stage II clinical trials.

Alterations in PKC, as well alterations in calcium regulation and potassium ($K^+$) channels are included among alterations in fibroblasts in Alzheimer's disease (AD) patients. PKC activation has been shown to restore normal $K^+$ channel function, as measured by TEA-induced $[Ca^{2+}]$ elevations. Further patch-clamp data substantiates the effect of PKC activators on restoration of 113ps$K^+$ channel activity. Thus PKC activator-based restoration of $K^+$ channels has been established as an approach to the investigation of AD pathophysiology, and provides a useful model for AD therapeutics. (See, pending U.S. application Ser. No. 09/652,656, which is incorporated herein by reference in its entirety.)

Of particular interest are macrocyclic lactones (i.e. bryostatin class and neristatin class) that act to stimulate PKC. Of the bryostatin class compounds, bryostatin-1 has been shown to activate PKC and proven to be devoid of tumor promotion activity. Bryostatin-1, as a PKC activator, is also particularly useful since the dose response curve of bryostatin-1 is biphasic. Additionally, bryostatin-1 demonstrates differential regulation of PKC isozymes, including PKCα, PKCδ, and PKCε. Bryostatin-1 has undergone toxicity and safety studies in animals and humans and is actively being investigated as an anti-cancer agent. Bryostatin-1's use in the studies has determined that the main adverse reaction in humans is myalgia, limiting the maximum dose to 40 mg/m². The present invention has utilized concentrations of 0.1 nM of bryostatin-1 to cause a dramatic increase of sAPP secretion. Bryostatin-1 has been compared to a vehicle alone and to another PKC activator, benzolactam (BL), used at a concentration 10,000 times higher. Bryostatin is currently in clinical trials as an anti-cancer agent. The bryostatins are known to bind to the regulatory domain of PKC and to activate the enzyme. Bryostatin is an example of isozyme-selective activators of PKC. Compounds in addition to bryostatins have been found to modulate PKC. (See, for example, WO 97/43268; incorporated herein by reference in its entirety).

Macrocyclic lactones, and particularly bryostatin-1 is described in U.S. Pat. No. 4,560,774 (incorporated herein by reference in its entirety). Macrocyclic lactones and their derivatives are described elsewhere in the art for instance in U.S. Pat. No. 6,187,568, U.S. Pat. No. 6,043,270, U.S. Pat. No. 5,393,897, U.S. Pat. No. 5,072,004, U.S. Pat. No. 5,196,447, U.S. Pat. No. 4,833,257, and U.S. Pat. No. 4,611,066 (each of which are incorporated herein by reference in their entireties). The above patents describe various compounds and various uses for macrocyclic lactones including their use as an anti-inflammatory or anti-tumor agent. Other discussions regarding bryostatin class compounds can be found in: Szallasi et al. (1994) Differential Regulation of Protein Kinase C Isozymes by Bryostatin 1 and Phorbol 12-Myristate 13-Acetate in NIH 3T3 Fibroblasts, *Journal of Biological Chemistry* 269(3): 2118-24; Zhang et al. (1996) Preclinical Pharmacology of the Natural Product Anticancer Agent Bryostatin 1, an Activator of Protein Kinase C, *Cancer Research* 56: 802-808; Hennings et al. (1987) Bryostatin 1, an activator of protein kinase C, inhibits tumor promotion by phorbol esters in SENCAR mouse skin, *Carcinogenesis* 8(9): 1343-46; Varterasian et al. (2000) Phase II Trial of Bryostatin 1 in Patients with Relapse Low-Grade Non-Hodgkin's Lymphoma and Chronic Lymphocytic Leukemia, *Clinical Cancer Research* 6: 825-28; and Mutter et al. (2000) Review Article: Chemistry and Clinical Biology of the Bryostatins, *Bioorganic & Medicinal Chemistry* 8: 1841-1860 (each of which is incorporated herein by reference in its entirety).

Myalgia is the primary side effect that limits the tolerable dose of a PKC activator. For example, in phase II clinical trials using bryostatin-1, myalgia was reported in 10 to 87% of all treated patients. (Clamp et al. (2002) *Anti-Cancer Drugs* 13: 673-683). Doses of 20 μg/m² once per week for 3 weeks were well tolerated and were not associated with myalgia or other side effects. (Weitman et al. (1999) *Clinical Cancer Research* 5: 2344-2348). In another clinical study, 25 μg/m² of bryostatin-1 administered once per week for 8 weeks was the maximum tolerated dose. (Jayson et al. (1995) *British J. of Cancer* 72(2): 461-468). Another study reported that 50 μg/m² (a 1 hour i.v. infusion administered once every 2 weeks for a period of 6 weeks) was the maximum-tolerated dose. (Prendville et al. (1993) *British J. of Cancer* 68(2): 418-424). The reported myalgia was cumulative with repeated treatments of bryostatin-1 and developed several days after initial infusion. Id. The deleterious effect of myalgia on a patient's quality of life was a contributory reason for the discontinuation of bryostatin-1 treatment. Id. The etiology of bryostatin-induced myalgia is uncertain. Id.

The National Cancer Institute has established common toxicity criteria for grading myalgia. Specifically, the criteria are divided into five categories or grades. Grade 0 is no myalgia. Grade 1 myalgia is characterized by mild, brief pain that does not require analgesic drugs. In Grade 1 myalgia, the patient is fully ambulatory. Grade 2 myalgia is characterized by moderate pain, wherein the pain or required analgesics interfere with some functions, but do not interfere with the activities of daily living. Grade 3 myalgia is associated with severe pain, wherein the pain or necessary analgesics severely interfere with the activities of daily living. Grade 4 myalgia is disabling.

The compositions of the present invention increase the tolerable dose of the PKC activator administered to a patient and/or ameliorate the side effects associated with PKC activation by attenuating the activation of PKC in peripheral tissues. Specifically, PKC inhibitors inhibit PKC in peripheral tissues or preferentially inhibit PKC in peripheral tissues. Vitamin E, for example, has been shown to normalize diacylglycerol-protein kinase C activation in the aorta of diabetic rats and cultured rat smooth muscle cells exposed to elevated glucose levels. (Kunisaki et al. (1994) Diabetes 43(11): 1372-1377). In a double-blind trial of vitamin E (2000 IU/day) treatment in patients suffering from moderately advanced Alzheimer's Disease, it was found that vitamin E treatment reduced mortality and morbidity, but did not enhance cognitive abilities. (Burke et al. (1999) *Post Graduate Medicine* 106(5): 85-96).

Macrocyclic lactones, including the bryostatin class were originally derived from *Bigula neritina L*. While multiple uses for macrocyclic lactones, particularly the bryostatin class are known, the relationship between macrocyclic lactones and cognition enhancement was previously unknown.

The examples of the compounds that may be used in the present invention include macrocyclic lactones (i.e. bryostatin class and neristatin class compounds). While specific embodiments of these compounds are described in the examples and detailed description, it should be understood that the compounds disclosed in the references and derivatives thereof could also be used for the present compositions and methods.

As will also be appreciated by one of ordinary skill in the art, macrocyclic lactone compounds and their derivatives, particularly the bryostatin class, are amenable to combinatorial synthetic techniques and thus libraries of the compounds can be generated to optimize pharmacological parameters, including, but not limited to efficacy and safety of the compositions. Additionally, these libraries can be assayed to determine those members that preferably modulate α-secretase and/or PKC.

Synthetic analogs of bryostatin are also contemplated by the present invention. Specifically, these analogues retain the orientation of the C1-, C19-, C26-oxygen recognition domain as determined by NMR spectroscopic comparison with bryostatin and various degrees of PKC-binding affinity. The bryostatin analogues disclosed and described in U.S. Pat. No. 6,624,189 (incorporated herein by reference in its entirety) may also be used in the methods of the present invention. Specifically, the bryostatin analogues described by the genus of Formula I of U.S. Pat. No. 6,624,189 (column 3, lines 35-66) and the species of formulas II-VII and 1998a and 1998b (column 8, lines 28-60) of U.S. Pat. No. 6,624,189 are PKC activators suitable for use in the methods of the present invention.

There still exists a need for the development of methods for the treatment for improved overall cognition, either through a specific characteristic of cognitive ability or general cognition. There also still exists a need for the development of methods for the improvement of cognitive enhancement whether or not it is related to specific disease state or cognitive disorder. The methods and compositions of the present invention fulfill these needs and will greatly improve the clinical treatment for Alzheimer's disease and other neurodegenerative diseases, as well as, provide for improved cognitive enhancement. The methods and compositions also provide treatment and/or enhancement of the cognitive state through the modulation of α-secretase.

EXAMPLES

Example 1

Behavioral Pharmacology

Bryostatin exposure—Specimens of *Hermissenda Crassicornis* were maintained in artificial sea water (ASW) at 15° for three days in perforated 50-ml conical centrifuge tubes before starting experiments. Bryostatin, purified from the marine bryozoan *Bugula neritina*, was dissolved in EtOH and diluted to its final concentration in ASW. Animals were incubated with bryostatin in ASW for 4 hr, then rinsed with normal ASW. For selected experiments lactacysteine (10 μM) or anisomycin was added to the ASW.

Bryostatin effects on *Hermissenda* behavior and biochemistry were produced by adding the drug to the bathing medium within an 8 cm long, 1 cm diameter test tube housing each individual animal.

Example 2

Immunostaining Methods

Following experimental treatments and testing, animals were rapidly decapitated, the central nervous systems (CNS) removed and then fixed in 4% para-formaldehyde in 20 mM Tris-buffered (pH 8) natural seawater (NSW; 0.2 μm micropore-filtered). The CNSs were then embedded in polyester wax (20), sectioned (6 μm) and immunostained using a biotinylated secondary antibody coupled to avidin-bound microperoxidase (ABC method, Vector), Aminoethylcarbazole (AEC) was used as the chromogen. The primary polyclonal antibody (designated 25U2) was raised in rabbits from the full length calexcitin protein extracted from squid optic lobes. Gray-scale intensity measures were done from digital photomicrographs on circumscribed cytoplasmic areas of the B-photoreceptors minus the same background area (non-staining neuropile).

Example 3

Protein Kinase C Assay

Cells were homogenized by sonication (5 sec, 25 W) in 100 μl of 10 mM Tris-HCl pH 7.4 buffer containing 1 mM EGTA, 1 mM PMSF, and 50 mM NaF. Homogenate was transferred to a polyallomer centrifuge tube and was centrifuged at 100,000×g for 10 min at 4°. The supernatant was removed and immediately frozen on dry ice. The particulate fraction was resuspended by sonication in 100 μl of the same buffer and stored at −80°. To measure PKC, 10 μl of cytosol or particulate fraction was incubated for 15 min at 37° in the presence of 10 μM histones, 4.89 mM $CaCl_2$, 1.2 μg/μl phosphatidyl-L-serine, 0.18 μg/μl 1,2-dioctanoyl-sn-glycerol, 10 mM $MgCl_2$, 20 mM HEPES (pH 7.4), 0-8 mM EDTA, 4 mM EGTA, 4% glycerol, 8 μg/ml aprotinin, 8 μg/ml leupeptin, and 2 mM benzamidine. 0.5 μCi [$\gamma^{32}$P]ATP was added and $^{32}$P-phosphoprotein formation was measured by adsorption onto phosphocellulose as described previously (25). This assay was used with slight adjustments for either *Hermissenda* nervous system homogenates or cultured mammalian neuron homogenates Example 4

Cell Culture

Rat hippocampal H19-7/IGF-IR cells (ATCC) were plated onto poly-L-lysine coated plates and grown at 35° in DMEM/10% FCS for several days until approx. 50% coverage was obtained. The cells were then induced to differentiate into a neuronal phenotype by replacing the medium with 5 ml N2 medium containing 10 ng/ml basic fibroblast growth factor and grown in T-25 flasks at 39° C. (26). Various concentrations of bryostatin (0.01-1.0 nM) were then added in 10 μl aqueous solution. After a specified interval, the medium was removed and the cells were washed with PBS, removed by gentle scraping, and collected by centrifugation at 1000 rpm for 5 min.

Example 5

Behavioral Conditioning

Figure 1:
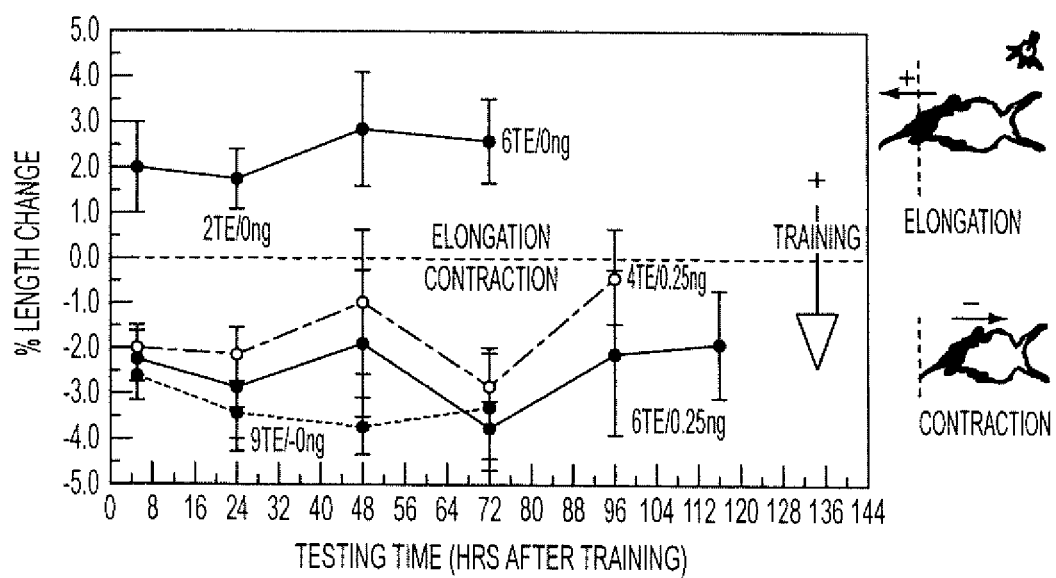
FIG. 1 depicts the effects of bryostatin on long term memory acquisition, and shows that animals trained suboptimally, but treated with bryostatin, all demonstrate acquisitioned long-term memory. Animals were trained with suboptimal regimes of 4- and 6-paired CS/US training events (TEs) with bryostatin (0.25 ng/ml) added during dark adaptation (10 min) prior to training and remaining for 4 hours, or without Bryo (NSW controls); 9-paired TEs and NSW served as the positive controls. Animals were tested with the CS alone at 4 h, then at 24-h intervals. Animals trained suboptimally but treated with bryostatin all demonstrated long-term retention (n=8-16 animals/condition/experiment; ANOVA, $p<0.01$).

Pavlovian conditioning of *Hermissenda* involves repeated pairings of a neutral stimulus, light, with an unconditioned stimulus, orbital shaking. (See, Lederhendler et al. (24) and Epstein et al. (6)). A rotation/shaking stimulus excites the statocyst hair cells and thereby elicits an unconditioned response: a brisk contraction of the muscular undersurface called a foot, accompanied by adherence or "clinging" to the surface that supports the foot. Before conditioning, light elicits a weakly positive phototaxis accompanied by lengthening of the foot. After sufficient light-rotation pairings, light no longer elicits phototaxis, but instead elicits a new response (24): the "clinging" and foot shortening previously elicited only by the unconditional stimulus (FIG. 1). Thus, the meaning of the unconditioned stimulus, rotation or orbital shaking, has been transferred to the conditioned stimulus and is manifested by a light-elicited foot contraction—a negative change of foot length. This conditioned response to light can last for weeks, is not produced by randomized light and rotation, is stimulus-specific, and shares the other defining characteristics of mammalian Pavlovian Conditioning.

Example 6

Bryostatin-Induced Prolongation of Associative Memory

Pavlovian conditioning of *Hermissenda* has well-defined training parameters that produce progressively longer-lasting retention of the learned conditioned response. Two training events (2 TE) of paired light and orbital shaking (see "Methods"), for example, induce a learned conditioned response (light-elicited foot contraction or shortening) that persists without drug treatment for approximately 7 minutes. Four to six training events (4-6 TE) induce a conditioned response that persists up to several hours, but disappears approximately by 1 day after training. Nine TE produces long-term associative memory lasting many days and often up to two weeks.

Animals were trained with sub-optimal regimes of 4- and 6-paired CS/US training events (TEs) with bryostatin (0.25 ng/ml) added during dark adaptation (10 min) prior to training and remaining for 4 hours, or without Bryo (NSW controls); 9-paired TEs and NSW served as the positive controls. All animals were tested with the CS alone at 4 h, then at 24-h intervals. Animals trained sub-optimally but treated with bryostatin all demonstrated long-term retention (n=8-16 animals/condition/experiment; ANOVA, p<0.01).

Two TE plus bryostatin produced memory retention lasting hours (vs. minutes without bryostatin), 4 TEs plus bryostatin extended retention beyond 24 hours (FIG. 1), and 6 TE plus bryostatin produced retention lasting 1 week or longer.

Figure 2:
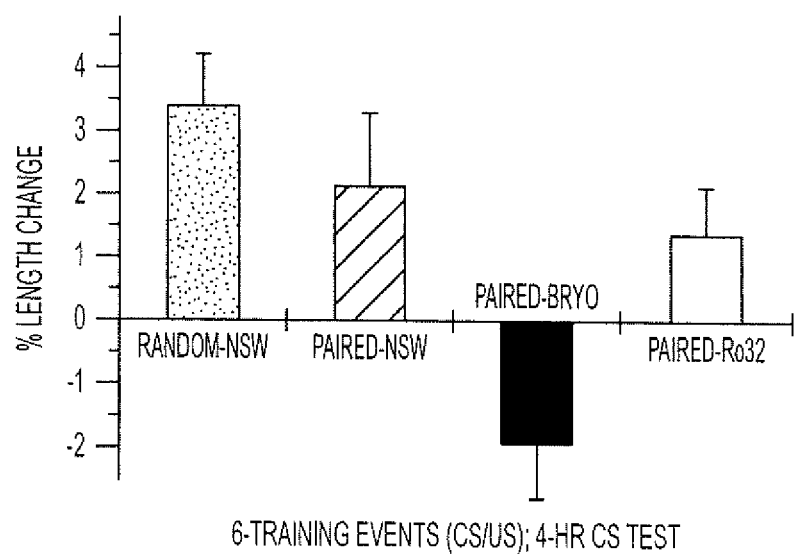
FIG. 2 depicts the effects of bryostatin on long-term memory acquisition, and shows that randomized presentations of light and rotation, either with or without bryostatin, produced no conditioned response. Long-term memory (LTM) retention effects of Bryostatin under control and antagonist experimental regimes. Without Bryostatin (NSW), random, and paired CS/US training events (TEs) did not generate LTM or elicit a CR when tested at 4 h. Bryostatin (0.25 ng/ml in NSW) applied before 6-TE conditioning (during 10 min dark adaptation) and for 4 hours thereafter produced a positive CR (foot contraction; negative change in length), thus indicating LTM was established. The antagonist, Ro-32 when applied pre-training (during dark adaptation), blocked the effects of 6TE plus bryostatin, i.e. animals lengthened (positive length change) with normal photaxis (n=4-8 animals/condition/experiment; ANOVA differences, $p<0.01$).

Without Bryostatin (NSW), random, and paired CS/US training events (TEs) did not generate LTM or elicit a CR when tested at 4 h. Bryostatin (0.25 ng/ml in NSW) applied before 6-TE conditioning (during 10 min dark adaptation) and for 4 hours thereafter produced a positive CR (foot contraction; negative change in length), thus indicating LTM was established. The antagonist, Ro-32 when applied pre-training (during dark adaptation), blocked the effects of 6 TE plus bryostatin, i.e. animals lengthened (positive length change) with normal phototaxis (n=4-8 animals/condition/experiment; ANOVA differences, p<0.01). Randomized presentations of light and rotation, with or without bryostatin, produced no conditioned response (FIG. 2), i.e., light-elicited foot-contraction. Thus, bryostatin during and immediately following training prolonged memory retention with sub-optimal training trials.

Example 7

Pre-Exposure to Bryostatin on Days Before Training Enhances Memory Acquisition Previous measurements (15, 17) have indicated that learning-induced PKC association with neuronal membranes (i.e., translocation) can be sustained. Rabbit nictitating membrane conditioning, rat spatial maze learning, maze learning, and rat olfactory discrimination learning have all been found to be accompanied by PKC translocation that lasts for days following training. *Hermissenda* conditioning was followed for at least one day after training by PKC translocation that could be localized in single, identifiable Type B cells (15).

Figure 3:
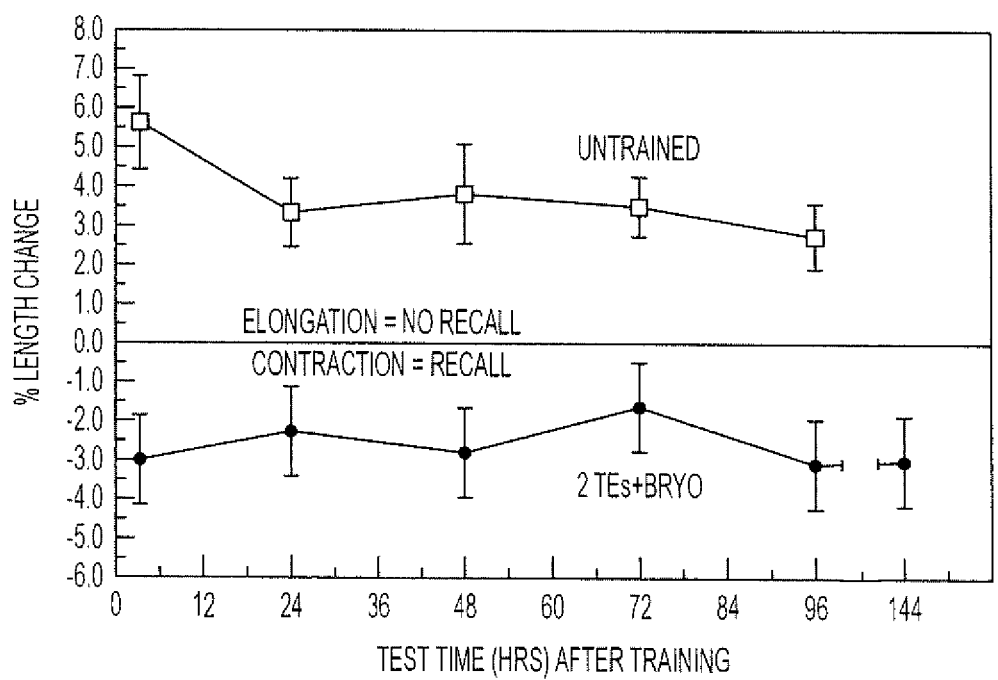
FIG. 3 depicts the effects of bryostatin on long-term memory acquisition, and shows that animals exposed to bryostatin for four hours on two successive days, followed by two training events (TE) on a third subsequent day, demonstrated acquisition of at least six days of long-term memory. Two successive days of 4-h bryostatin exposure (0.25 ng/ml) of animals coupled with 2-paired CS/US training events produced at least 6 days of long-term retention demonstrated by the CR (body length contraction) when tested with the CS alone (n=16 animals/condition; ANOVA, $p<0.01$).

As already described, exposure to bryostatin for 4 hours during and after training enhances memory retention produced by 2 TE from 6-8 minutes to several hours. However, a 4 hour exposure to bryostatin on the day preceding training, as well as on the day of the 2 TE prolonged memory retention for more than one day after training. Two successive days of 4-h bryostatin exposure (0.25 ng/ml) of animals coupled with 2-paired CS/US training events produced at least 6 days of long-term retention demonstrated by the CR (body length contraction) when tested with the CS alone (n=16 animals/condition; ANOVA, p<0.01) (FIG. 3).

Figure 4:
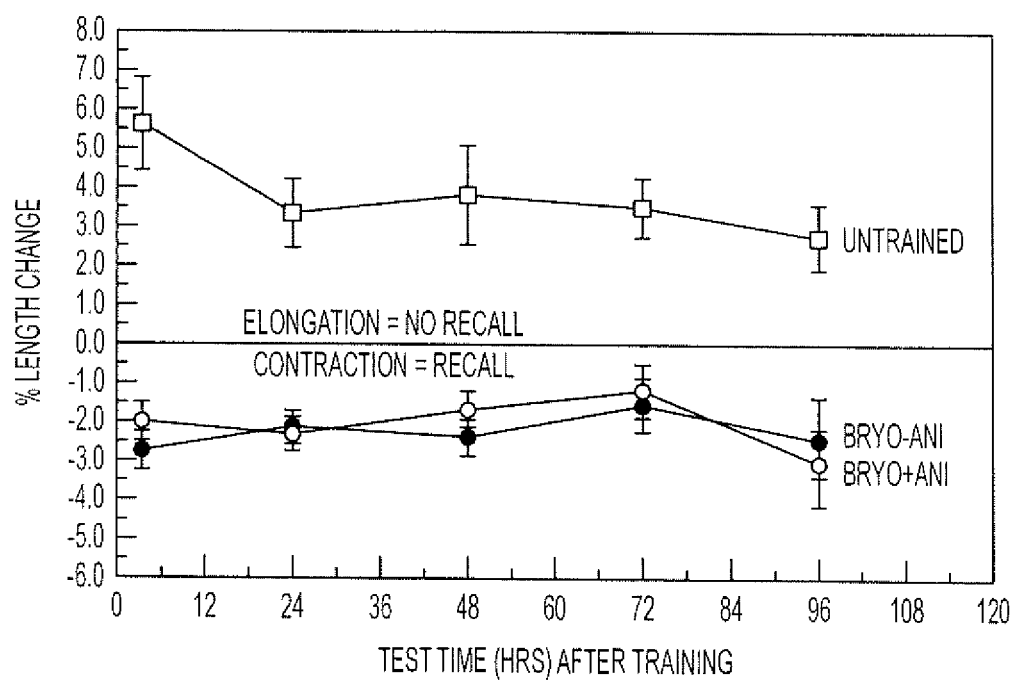
FIG. 4 depicts the effects of bryostatin on long term memory acquisition, and shows that animals exposed to bryostatin for four hours on three successive days, followed by two TE on a fourth subsequent day, demonstrated acquisition of at least ninety-six hours of long-term memory. Animals given three successive days of 4-h bryostatin exposure (0.25 ng/ml) followed one day later by 2-TEs, demonstrated long-term retention (LTR) measured over 96 h post-training. Non-exposed animals (same as in FIG. 3) did not demonstrate any behavioral modification (no CR to CS testing). Anisomycin (ANI) (1 µg/ml) administered immediately and remaining for four hours post-training to animals receive the three-day bryostatin treatments did not prevent long-term retention. Thus the requirement for protein synthesis necessary to generate LTR that is usually blocked by ANT when added post-training was obviated by the three-day bryostatin treatment (n=16 animals/condition; ANOVA, $p<0.01$).
Figure 5:
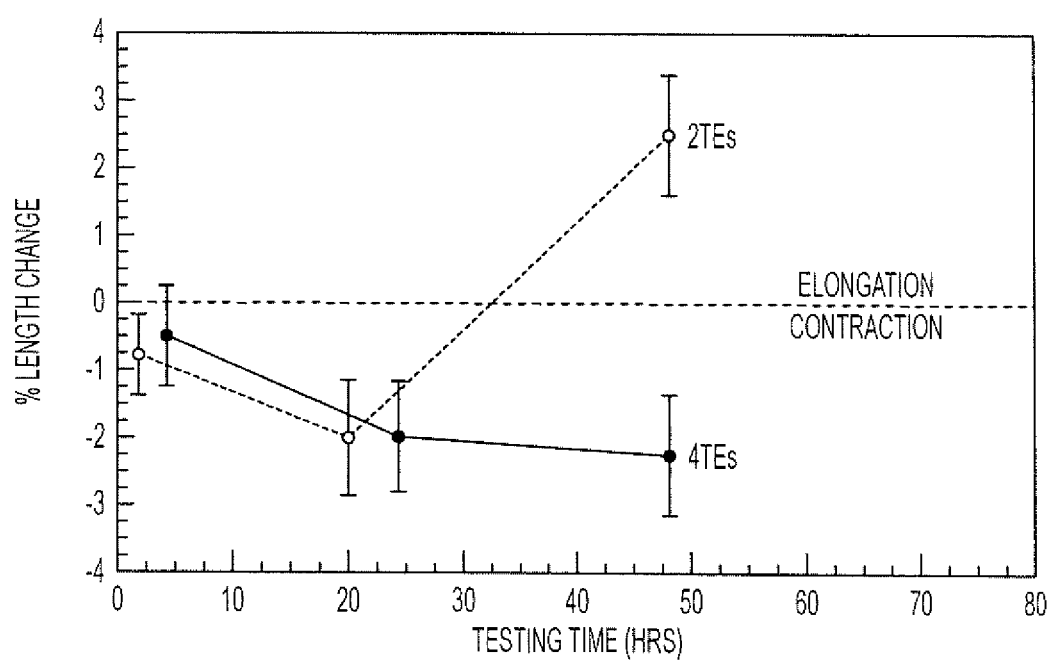
FIG. 5 depicts the effects of bryostatin on long term memory acquisition, and shows that exposure to bryostatin for 8 to 20 hours followed by two TE was not sufficient to acquire memory equivalent to that achieved after a 4-hour exposure to bryostatin. Effects of 20 hr Bryostatin (0.25 ng/ml) exposure on training. With the sub-optimal 2-paired TE conditioning regime, retention was gone in 48 hours. Retention of 4-paired TE conditioning with 20 h pre-exposure to bryostatin persisted (n=8 animals/condition; ANOVA at 48-h, $p<0.01$).

Animals given three successive days of 4-h bryostatin exposure (0.25 ng/ml) followed one day later by 2-TEs, demonstrated long-term retention (LTR) measured over 96 h post-training. Non-exposed animals (same as in FIG. 3) did not demonstrate any behavioral modification (no CR to CS testing). Anisomycin (ANI) (1 µg/ml) administered immediately and remaining for four hours post-training to animals receiving the three-day bryostatin treatments did not prevent long-term retention. Thus the requirement for protein synthesis necessary to generate LTR that is usually blocked by ANI when added post-training was obviated by the three-day bryostatin treatment (n=16 animals/condition; ANOVA, p<0.01). A third day of exposure to the 4 hour interval of bryostatin caused a similar enhanced retention of the Pavlovian conditioned response (FIG. 4). The preceding results support the view that two successive intervals of exposure to bryostatin cause PKC activation and possibly synthesis of proteins critical for long-term memory, with a minimum of concurrent and subsequent PKC downregulation. This view was given further support by the observation that a more prolonged interval of bryostatin exposure, i.e. for 8 to 20 hours, followed by 2 TE (FIG. 5) was not sufficient itself to produce memory retention equivalent to that which accompanied the two 4 hour exposures on successive preceding days. In these experiments, the effects of 20 hr bryostatin (0.25 ng/ml) exposure on training was observed. With the sub-optimal 2-paired TE conditioning regime, retention was gone in 48 hours. Retention of 4-paired TE conditioning with 20 h pre-exposure to bryostatin persisted (n=8 animals/condition; ANOVA at 48-h, p<0.01). Sufficiently prolonged bryostatin exposure (e.g., 8-12 hours) is known in other cell systems to cause prolonged PKC downregulation that may offset PKC activation and increase PKC synthesis.

Figure 6:
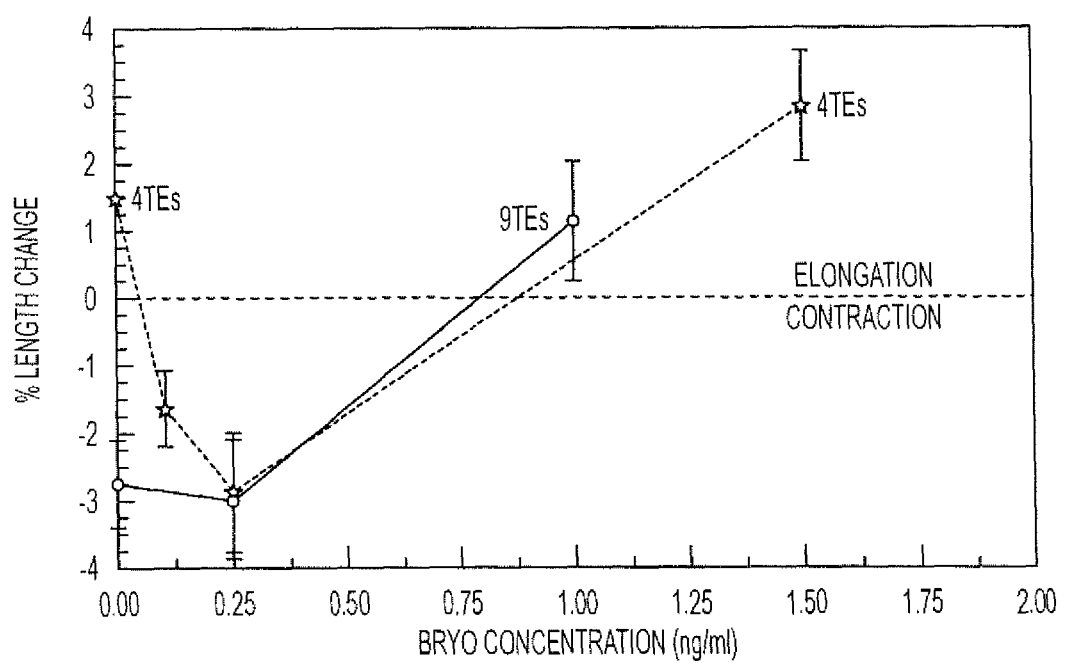
FIG. 6 depicts the effects of bryostatin on long term memory acquisition, and shows that exposure to more than 1.0 ng/ml of bryostatin inhibits acquisition of long-term memory. Retention dose-response curves for 4- and 9-paired CS/US training events. Bryostatin concentrations <0.50 ng/ml augment acquisition and memory retention with sub-optimal (4 TE) training conditions. Those concentrations had no demonstrable effects on retention performance with 9-paired TEs. However, with all training conditions tested, concentration ≥1.0 ng/ml inhibited acquisition and behavioral retention (n=16 animals/condition), presumably via PKC down regulation.

Similarly, sufficiently increased concentrations of bryostatin ultimately blocked memory retention (FIG. 6) presumably also because of PKC downregulation. Bryostatin concentrations <0.50 ng/ml augment acquisition and memory retention with sub-optimal (4 TE) training conditions. Those concentrations had no demonstrable effects on retention performance with 9-paired TEs. However, with all training conditions tested, concentration ≥1.0 ng/ml inhibited acquisition and behavioral retention (n=16 animals/condition), presumably via PKC downregulation.

Example 8

Figure 7:
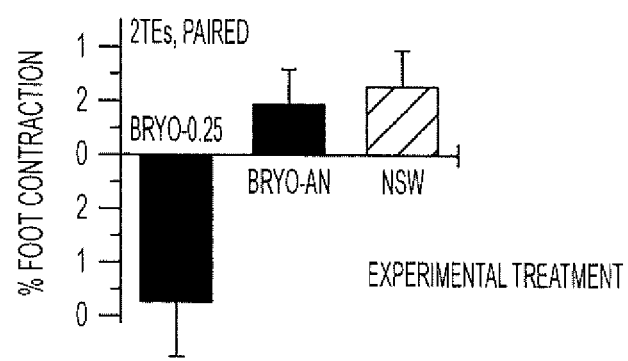
FIG. 7 depicts the effects of bryostatin and anisomycin on long-term memory acquisition, and shows that a single 4-hour exposure to bryostatin together with 2 TE produced long-term memory lasting hours that was entirely eliminated when anisomycin was present during bryostatin exposure. Bryostatin and anisomycin effects on behavioral acquisition and retention. Animals received 2-paired training events (TEs) and then tested for retention after 4 h. Bryostatin (0.25 ng/ml) applied in NSW to animals during the 10-min pre-training dark adaptation period and 4 h thereafter demonstrated retention of the behavioral conditioning (foot contraction (CR) and shortening in body length). NSW control animals and those treated with bryostatin pre-training followed by anisomycin (1.0 µg/ml) immediately post-training showed no CR with the foot lengthening in normal positive phototaxis (n=12 animals/condition/experiment, two-way ANOVA statistics, $p<0.01$).

Pre-Exposure to Bryostatin Obviates the Requirement for Protein Synthesis During Training Animals received 2-paired training events (TEs) and then tested for retention after 4 h. Bryostatin (0.25 ng/ml) applied in NSW to animals during the 10-min pre-training dark adaptation period and 4 h thereafter demonstrated retention of the behavioral conditioning (foot contraction (CR) and shortening in body length). NSW control animals and those treated with bryostatin pre-training followed by anisomycin (1.0 µg/ml) immediately post-training showed no CR with the foot lengthening in normal positive phototaxis (n=12 animals/condition/experiment, two-way ANOVA statistics, $p<0.01$). A single 4 hour exposure to bryostatin together with 2 TE produced long-term memory retention lasting hours that was entirely eliminated when anisomycin was present along with the bryostatin (FIG. 7). Similar blocking effects of anisomycin were also observed with 6 TE plus bryostatin. Repeated brief exposures to bryostatin, however, increase the net synthesis of PKC, calexcitin, and other memory proteins and thus eliminate the requirement for new synthesis during and after Pavlovian conditioning—if PKC downregulation were sufficiently minimized. Protein synthesis was blocked for 4 hours with anisomycin immediately after 2 TE of animals that on each of 3 preceding days had been first exposed to 4 hours of bryostatin. In this case, anisomycin-induced blockade of protein synthesis did not prevent memory retention that lasted many days (FIG. 4). By contrast, the same 4 hour anisomycin treatment eliminated all memory retention produced by 9 TE, a training regimen ordinarily followed by 1-2 weeks of memory retention (27). Finally, if 2 TE were given one day after three successive days of 4 hour exposures to bryostatin that was accompanied each time by anisomycin, long-term memory was eliminated.

Example 9

Pre-Exposure to Proteasome Inhibition Enhances Bryostatin Effects on Memory

Another means of enhancing and prolonging de novo synthesis of PKC and other memory-related proteins is provided by blocking pathways involved in protein degradation. One of these, the ubiquitin-proteasome pathway (28-30), is known to be a major route for degradation of the α-isozyme of PKC. Degradation of PKC-α has been previously shown to be largely prevented by 20 µM-5 QµM of the proteasome inhibitor, Lactacysteine.

Figure 8:
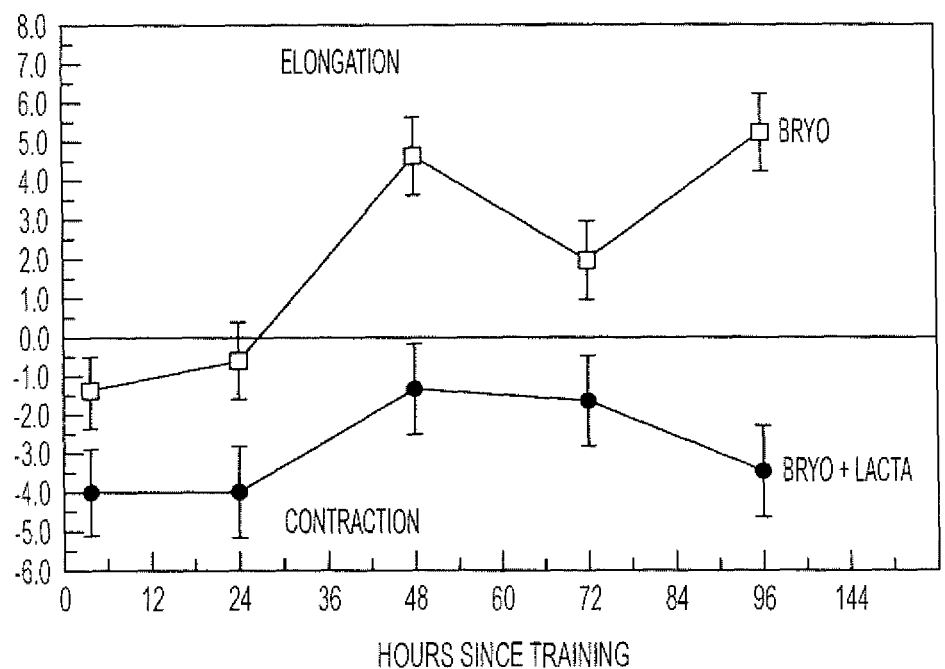
FIG. 8 depicts the effects of bryostatin and lactacysteine, and shows that lactacysteine transformed the short-term memory produced by the single bryostatin exposure (followed by 2 TE) to long-term memory lasting many days. Behavioral effects of bryostatin and lactacystin. Animals were incubated simultaneously for 4 h with bryostatin (0.25 ng/ml) and lactacystin (10 µM), and then 24 hrs later were conditioned with 2-paired CS/US training events (TEs). Animals were subsequently tested with CS alone at 4 h post-training and then at 24-h intervals. Retention of the conditioned behavior was persistent with the combined bryostatin/lactacystin treatment; behavioral retention was lost by bryostatin-only-treated animals after 24 h. Lactacystin-only treated animals showed no acquisition or retention of behavioral training (data not graphed). (n=28 animals, combined byrostatin/lactacystin; n=20, bryostatin alone, n=16, lactacystin alone).
Figure 9A:
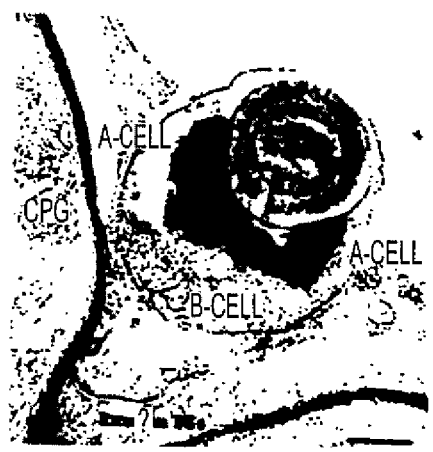
FIG. 9 depicts the effects of PKC activation on calexcitin. Figures (A, B) depict representative tissue sections from *Hermissenda* eyes that were immunolabeled with the calexcitin polyclonal antibody, 25U2. Positive claexcitin immunostaining occurred in B-cell photoreceptors (*B-Cell) of animals that experienced paired CS/USC associative conditioning with or without prior administration of bryostatin (B). Random presentations of the two stimuli (training events, TEs) did not produce behavioral modifications nor a rise in calexcitin above normal background levels (A); basement membrane and lens staining are artifact associated with using vertebrate polyclonal antibodies. Differences in staining intensities were measure using Image-J software and recorded as gray-scale intensities (0-256; B-cell cytoplasm minus tissue background).
Figure 9B:
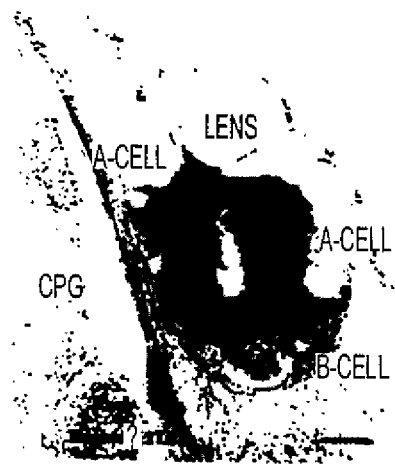
Figure 9C:
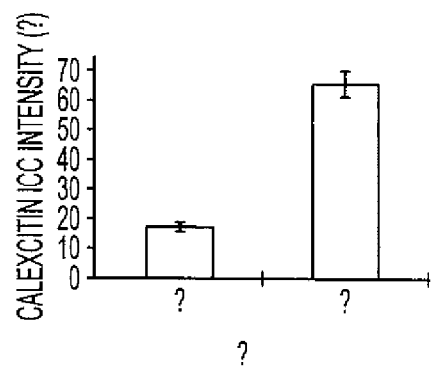
Figure 9D:

Animals were incubated simultaneously for 4 h with bryostatin (0.25 ng/ml) and lactacysteine (10 µM), and then 24 hrs later were conditioned with 2-paired CS/US training events (TEs). Animals were subsequently tested with the CS alone at 4 h post-training and then at 24-h intervals. Retention of the conditioned behavior was persistent with the combined bryostatin/lactacysteine treatment; behavioral retention was lost by bryostatin-only-treated animals after 24 h. Lactacysteine-only treated animals showed no acquisition or retention of behavioral training (data not graphed). (n=28 animals, combined bryostatin/lactacysteine; n=20, bryostatin alone; n=16, lactacysteine alone). Lactacysteine, in this case, transformed the short-term memory produced by the single bryostatin exposure (followed by 2 TE) to long-term memory lasting many days (FIG. 8).

Example 10

Calexcitin-Immunostaining Due to PKC Activation

Recently we showed that an immunostaining label of calexcitin increased within single identified Type B cells during acquisition and retention of *Hermissenda* conditioning (20). Many previous findings have implicated a low molecular weight calcium and GTP-binding protein, calexcitin, as a substrate for PKC isozymes during *Hermissenda* conditioning (19). Calexcitin, now completely sequenced in some animal species, and shown to have significant homology with similar proteins in other species (31), undergoes changes of phosphorylation during and after *Hermissenda* Pavlovian conditioning. It is also a high affinity substrate for the alpha-isozyme of PKC and a low affinity substrate for β and gamma (19).

Micrographs (A, B) depict representative tissue sections from *Hermissenda* eyes that were immunolabeled with the calexcitin polyclonal antibody, 25U2. Positive calexcitin immunostaining occurred in B-cell photoreceptors (*B-Cell) of animals that experienced paired CS/UCS associative conditioning with or without prior administration of bryostatin (B). Random presentations of the two stimuli (training events, TEs) did not produce behavioral modifications nor a rise in calexcitin above normal background levels (A); basement membrane and lens staining are artifact associated with using vertebrate polyclonal antibodies. Differences in staining intensities were measured and recorded as gray-scale intensities (0-256; B-cell cytoplasm minus tissue background). Graph (C) displays intensity measures for *Hermissenda* conditioned with 9-random TEs (left bar) and animals treated with two exposures on successive days to the PKC agonist, bryostatin (0.25 ng/ml), and then associatively conditioned with 2-paired TEs. Activation of PKC from two exposures of bryostatin coupled with 2 TEs significantly increased calexcitin to levels associated with 9-paired TEs and consolidated (long-term) memory (n=4-8 animals/condition/replicate; t-test comparison, $p<0.01$).

Calexcitin immunostaining is sufficiently sensitive to resolve boutons within synaptic fields of photic-vestibular neurites (D). Arrows indicate arborization field between an interneuron (a), axon from a contralateral neuron (b), and terminal boutons of neurites from a putative photoreceptor (c). Scale bars=10 µm; cerebropleural ganglion (FIG. 9, 10).

This conditioning-induced calexcitin label increase represents an increase in the actual amount of the protein since the immunostaining antibody reacts with both the phosphorylated and unphosphorylated forms of the protein. PKC, previously shown to translocate within the same individual Type B cells, apparently caused the conditioning-induced increase in the calexcitin label since the specific PKC-blocker, Ro-32, prevented both learning and learning-specific calexcitin increases in the Type B cell (see above). Naïve and/or randomized control training protocols produced a small fraction of the training-induced calexcitin (CE) immunostaining (FIG. 9).

Random training (4-TEs) without bryostatin yielded slightly higher intensity measures than background. Bryostatin administration increased the calexcitin levels for both training paradigms. With random training, when there was occasional overlap (pairing) of the CS and US, as was the case here, it is not unexpected that some rise in CE might occur (increase of 2.0). However, calexcitin levels increased greater than 4.3× with paired training (mean±SE, N=5 animals/treatment. 4RTE=random control, 4 trials with random light and rotation; 6PTE=paired trials, 6 trials with paired light and rotation. 6PTE-OBry vs. 6PTE-0.25Bry: p<0.001; 4RTE-0.25Bry vs. 6PTE-0.25Bry; p<0.001 (t-test). When sub-optimal training events (4-6 TE) were used, the CE immunostaining (FIG. 10A) reached an intermediate level of elevation. These sub-optimal regimes were insufficient to produce memory retention lasting longer than 24 hours. As described earlier, bryostatin administered during training with 6 TE induced long-term memory retention (>1 week). Furthermore, bryostatin plus 6 TE induced CE immunostaining comparable to that observed after 9 TE.

Bryostatin in low doses (0.1-0.25 ng/ml) markedly enhanced memory after 2, 4, or 6 training trials. Pavlovian conditioning with 6 TE produced memory lasting many days with bryostatin, but lasting only hours without bryostatin. This memory enhancement was blocked by anisomycin or the PKC inhibitor, Ro-32. It is important to note that CE immunostaining was greatly reduced 24 hours after 9 TE even though the memory persisted for more than 1 week thereafter. More persistent CE immunostaining resulted, however, from repeated bryostatin exposures on days preceding minimal training (2 TE).

Bryostatin alone (without associative conditioning) administered for 4-hr over each of 1, 2, and 3 days progressively increased the levels of calexcitin in the B-photoreceptors of *Hermissenda* when measured 24 hours after each of the periods of bryostatin exposures. Twenty-four hours after 1 bryostatin exposure for four hours, CE immunostaining was not elevated (FIG. 10B). Twenty-four hours after 2 bryostatin exposures, 1 on each of two successive days showed greater residual CE immunostaining. The calexcitin level after 3 bryostatin exposures followed by just 2-paired training events (paired light and orbital shaking) raised that level even higher with a significant concomitant length in the number of retention days for the associative conditioning-induced behavioral modification (n=16 animals/condition: ANOVA, p<0.01). With 2 TE on the subsequent day after these three exposures, CE immunostaining 24 hours later approached the levels previously observed immediately following 9 TE (FIG. 10B). Thus, CE immunostaining following these three days of 4 hour bryostatin exposure followed by minimal training (2 TE) showed a greater persistence than did the training trials alone. This persistence of newly synthesized calexcitin is consistent with the biochemical observations indicating enhanced protein synthesis induced by bryostatin.

Exposure to 4-hr of bryostatin on two consecutive days followed 24 hours later by 2-training events (2 TE) are required to raise calexcitin levels to the amount associated with consolidated long-term memory. Typically, 2-TEs with two bryostatin exposures produces retention lasting more than one week (n=16 animals/condition; t-test, p<0.01). Priming with 4-hr exposures to bryostatin over 3 consecutive days will induce calexcitin levels required for consolidated memory. Anisomycin added immediately after the 2-paired training events did not reduce this calexcitin level and consolidated memory persists for many days (N=8 animals/condition; t-test, p>0.05, ns). (FIGS. 11A, B).

It is noteworthy that the Ro-32 inhibition of PKC immediately after bryostatin plus training did not prevent long-term memory induction, while this inhibition during the training plus bryostatin did prevent memory consolidation. In contrast, anisomycin during training with and without bryostatin did not prevent long-term memory, while anisomycin after training with and without bryostatin completely blocked memory formation. Therefore, PKC activation during training is followed by protein synthesis required for long-term memory. Thus, once PKC activation is induced to sufficient levels, the required protein synthesis is an inevitable consequence. Consistently, bryostatin-induced PKC activation on days prior to training is sufficient, with minimal training trials, to cause long-term memory. Furthermore, this latter long-term memory does not require protein synthesis following the training (and PKC activation on preceding days). Again, prior PKC activation was sufficient to produce that protein synthesis necessary for subsequent long-term memory formation. One of those proteins whose synthesis is induced by bryostatin-induced PKC activation as well as conditioning trials is calexcitin—as demonstrated by the immunostaining labeling. The other protein is PKC itself.

Example 11

Effect of Bryostatin on PKC Activity

Bryostatin is known to transiently activate PKC by increasing PKC association with the cellular membrane fraction. A variety of associative memory paradigms have also been demonstrated to cause increased PKC association with neuronal membranes. We tested, therefore, the possibility that repeated exposures of *Hermissenda* to bryostatin (i.e., 4 hour exposures, exactly as with the training protocols) might also induce prolonged PKC activation.

Intact *Hermissenda* were exposed for 4 hour intervals to bryostatin (0.28 nM) on successive days under conditions described ("Behavioral Pharmacology"). Histone phosphorylation (See "Methods") in isolated circumesophageal nervous systems was then measured in the cytosol fraction. PKC activity measured both 10 minutes and 24 hours after the second of two bryostatin exposures was significantly increased over baseline levels (N=6, for each measurement). (FIG. 12, 13). Thus, the quantity of PKC in both fractions was apparently increased, but not the ratio of the PKC in the membrane to that in the cytosolic fraction. These results demonstrate that the bryostatin pre-exposure causes an effect on PKC somewhat different from learning itself. After an initial activation (via translocation), this bryostatin effect is most likely due to increased synthesis of PKC, consistent with the increased levels of calexcitin induced by bryostatin, but not directly correlated with repeated bryostatin exposure.

As in FIG. 12, 13 but with anisomycin (1.0 ng/ml) added together with each bryostatin (0.25 ng/ml) exposure. Note that the anisomycin markedly reduced the PKC activity in both the cytosolic and membrane fractions from the *Hermissenda* circumesophageal nervous systems after exposure to bryostatin on three successive days (N=3, for each measurement, p<0.01) (FIG. 14).

To further examine biochemical consequences of repeated exposures to bryostatin, rat hippocampal neurons were studied after they had been immortalized by retroviral transduction of temperature sensitive tsA5CSV40 large T antigen (25). These differentiate to have a neuronal phenotype when induced by basic fibroblast growth factor in N2 medium (26) and express a normal complement of neuronal proteins, including PKC.

Exposure of cultured hippocampal neurons to a single activating dose of bryostatin (0.28 nM) for 30 minutes produced a brief translocation of PKC from the cytosol to the particulate fraction (approx 60%) followed by a prolonged downregulation (FIG. 15). Both the initial PKC activation and subsequent downregulation have been previously described and were confirmed by measurement of PKC activity in membrane and cytosol. Exposing the cultured hippocampal neurons to one 30-minute period of bryostatin, followed by a second 30-minute exposure, at intervals ranging from 30 minutes to 8 hours, caused the membrane-bound PKC to rebound more quickly. Thus, a second exposure after a 2- to 4-hour delay eliminated the significant downregulation that a single bryostatin exposure produced (FIG. 16). In the cytoplasmic fraction, no significant alteration of PKC activity was detected within the first 4 hours after bryostatin exposure. In contrast, if cells were exposed to bryostatin twice within a 2-hour period, there was a significant reduction of PKC activity in response to the second exposure. However, if the second exposure was delayed until 4 hours after the first, activity was increased above baseline, to a degree that was significantly greater compared with a second exposure delivered after 2 hours or less (FIG. 16).

These results are consistent with the interpretation that the initial bryostatin activation of PKC followed by downregulation (28-30) leads to increased synthesis (via de novo protein synthesis) of PKC isozymes (as well as calexcitin, described earlier). In fact, we found here that a single 30-minute exposure to 0.28 nM bryostatin increased overall protein synthesis (FIG. 17), measured by incorporation of $^{35}$-S Methionine in the last ½ hour before collecting the neurons, by 20% within 24 h, increasing to 60% by 79 hours after the bryostatin exposure. This prolonged and profound increase of protein synthesis induced by bryostatin was partially blocked when the PKC inhibitor Ro-32 was also present (FIG. 17).

Abundant observations indicate that sufficient bryostatin-induced PKC activation leads, inevitably, to progressive PKC inactivation and subsequent downregulation. Sufficient doses of bryostatin (greater than 1.0 ng/ml) actually inhibited Pavlovian conditioning. This was most likely due to PKC downregulation that characterized the behavioral results with high bryostatin concentrations. PKC activation induced by bryostatin has been shown to be downregulated by two distinct pathways. One that is also induced by phorbol ester involves ubiquitination and subsequent proteolytic degradation through the proteasome pathway. The second mechanism of downregulation, not induced by phorbol ester, involves movement through caveolar compartments and degradation mediated by phosphatase PP1 and PP2A. With sufficient concentrations and/or durations of PKC activators, the PKC degrading pathways create a deficit of PKC that stimulates de novo synthesis of PKC, PKC synthesis cannot compensate for inactivation and down regulation, thereby causing depletion of available PKC of 95% or more.

I claim:

1. A method for consolidating long term memory comprising: administering to a subject an effective amount of a PKC activator to activate PKC and minimize PKC downregulation; and subsequently administering a PKC inhibitor to the subject, wherein the PKC activator is bryostatin or neristatin, and wherein the PKC inhibitor is RO-32-0432.

2. The method according to claim 1, wherein the PKC activator is a bryostatin.

3. The method according to claim 2, wherein the bryostatin is chosen from bryostatin-1, -2, -3, -4, -5, -6, -7, -8, -9, -10, -11, -12, -13, -14, -15, -16, -17, and -18.

4. The method according to claim 3, wherein the bryostatin is bryostatin-1.

5. The method according to claim 1, wherein the PKC activator is neristatin.

6. The method according to claim 1, wherein administration of the PKC activator increases the synthesis of PKC.

7. The method according to claim 1, wherein administration of the PKC activator increases the amount of calexcitin.

* * * * *